(12) United States Patent
Fuchiwaki et al.

(10) Patent No.: US 11,655,211 B2
(45) Date of Patent: May 23, 2023

(54) POLYCYCLIC COMPOUND AND ORGANIC ELECTROLUMINESCENCE DEVICE INCLUDING THE SAME

(71) Applicant: Samsung Display Co., Ltd., Yongin-si (KR)

(72) Inventors: Junta Fuchiwaki, Yokohama (JP); Tohru Sato, Kyoto (JP)

(73) Assignee: Samsung Display Co., Ltd., Yongin-si (KR)

( * ) Notice: Subject to any disclaimer, the term of this patent is extended or adjusted under 35 U.S.C. 154(b) by 746 days.

(21) Appl. No.: 16/260,589

(22) Filed: Jan. 29, 2019

(65) Prior Publication Data

US 2019/0241519 A1  Aug. 8, 2019

(30) Foreign Application Priority Data

Feb. 2, 2018  (KR) .................. 10-2018-0013610

(51) Int. Cl.
*C07D 209/86* (2006.01)
*C07D 209/88* (2006.01)
(Continued)

(52) U.S. Cl.
CPC ......... *C07D 209/86* (2013.01); *C07D 209/88* (2013.01); *H01L 51/0054* (2013.01);
(Continued)

(58) Field of Classification Search
None
See application file for complete search history.

(56) References Cited

U.S. PATENT DOCUMENTS 7,538,250 B2   5/2009 Suzuki et al.
8,610,345 B2 * 12/2013 Murase ............... H01L 51/0054
                                                      313/504
(Continued)

FOREIGN PATENT DOCUMENTS

CN   103539725 A   1/2014
JP   2008-127291 A  6/2008
(Continued)

OTHER PUBLICATIONS

Childirala et al. J. Org. Chem. 2016, 81, 603-614.*

*Primary Examiner* — Clinton A Brooks
(74) *Attorney, Agent, or Firm* — Lewis Roca Rothgerber Christie LLP

(57) ABSTRACT

A polycyclic compound is represented by Formula 1:

(Continued)

where $X_1$, $R_1$ to $R_{11}$, $L_1$, $L_2$, and $n_1$ to $n_4$ are further defined. An organic electroluminescence device includes the polycyclic compound.

21 Claims, 2 Drawing Sheets

(51) Int. Cl.
    *H01L 51/50*     (2006.01)
    *H01L 51/00*     (2006.01)

(52) U.S. Cl.
    CPC ...... *H01L 51/0072* (2013.01); *H01L 51/5016* (2013.01); *H01L 51/5012* (2013.01)

(56) References Cited

U.S. PATENT DOCUMENTS

| | | |
|---|---|---|
| 8,916,275 B2 | 12/2014 | Nakano et al. |
| 9,859,503 B2 | 1/2018 | Hwang et al. |
| 2014/0027754 A1 | 1/2014 | Ueoka et al. |
| 2017/0029362 A1 | 2/2017 | Howard, Jr. et al. |

FOREIGN PATENT DOCUMENTS

| | | |
|---|---|---|
| JP | 5012998 B2 | 8/2012 |
| JP | 6020166 B2 | 11/2016 |
| KR | 10-2008-0055891 A | 6/2008 |
| KR | 10-2010-0075101 A | 7/2010 |
| KR | 10-1195655 B1 | 10/2012 |
| KR | 10-2014-0034771 A | 3/2014 |
| KR | 10-2015-0084562 A | 7/2015 |
| KR | 10-1616691 B1 | 4/2016 |
| KR | 10-1661925 B1 | 9/2016 |
| WO | 2007/029798 A1 | 3/2007 |
| WO | WO 2012/173073 A1 | 12/2012 |

\* cited by examiner

POLYCYCLIC COMPOUND AND ORGANIC ELECTROLUMINESCENCE DEVICE INCLUDING THE SAME

CROSS-REFERENCE TO RELATED APPLICATION

Korean Patent Application No. 10-2018-0013610, filed on Feb. 2, 2018, in the Korean Intellectual Property Office, and entitled: "Polycyclic Compound and Organic Electroluminescence Device Including the Same," is incorporated by reference herein in its entirety.

BACKGROUND

1. Field

Embodiments relate to a polycyclic compound and an organic electroluminescence device including the same.

2. Description of the Related Art

The development of an organic electroluminescence display device as an image display device is being actively conducted. Different from a liquid crystal display device, the organic electroluminescence display device is so-called a self-luminescent display device in which holes and electrons injected from a first electrode and a second electrode recombine in an emission layer, and a light-emitting material which is an organic compound included in the emission layer emits light to attain display.

As an organic electroluminescence device, an organic device including, for example, a first electrode, a hole transport layer disposed on the first electrode, an emission layer disposed on the hole transport layer, an electron transport layer disposed on the emission layer, and a second electrode disposed on the electron transport layer is well known. Holes are injected from the first electrode, and the injected holes move via the hole transport layer and are injected into the emission layer. Meanwhile, electrons are injected from the second electrode, and the injected electrons move via the electron transport layer and are injected into the emission layer. The holes and electrons injected into the emission layer recombine to produce excitons in the emission layer. The organic electroluminescence device emits light using light generated by the transition of the excitons to a ground state. In addition, various modifications may be made in the configuration of the organic electroluminescence device.

SUMMARY

Embodiments are directed to a polycyclic compound represented by the following Formula 1:

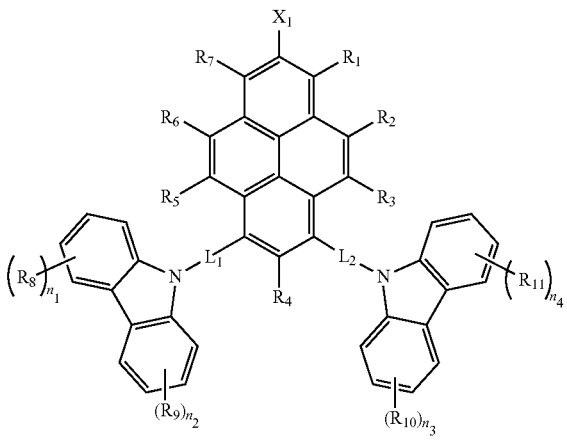

[Formula 1]

wherein, in Formula 1, $X_1$ is a substituted or unsubstituted alkyl group having 1 to 12 carbon atoms, or a substituted or unsubstituted silyl group, $R_1$ to $R_{11}$ are each independently a hydrogen atom, a deuterium atom, a halogen atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, $L_1$ and $L_2$ are each independently a substituted or unsubstituted arylene group having 6 to 30 ring carbon atoms, and "$n_1$" to "$n_4$" are each independently an integer of 0 to 4.

The polycyclic compound represented by Formula 1 may be represented by the following Formula 2:

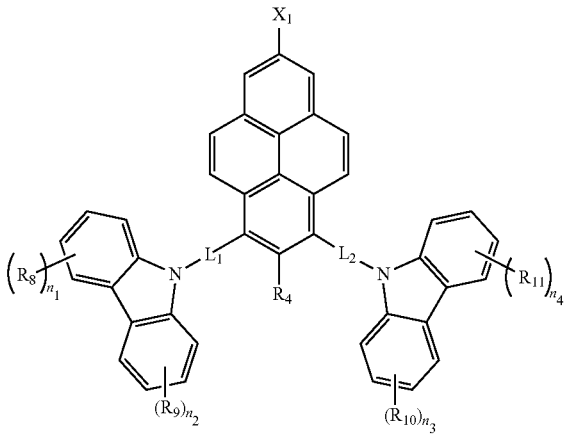

[Formula 2]

wherein in Formula 2, $X_1$, $L_1$, $L_2$, $R_8$ to $R_{11}$, and "$n_1$" to "$n_4$" are the same as defined in Formula 1.

The polycyclic compound represented by Formula 2 may be represented by one of the following Formula 3:

[Formula 3]

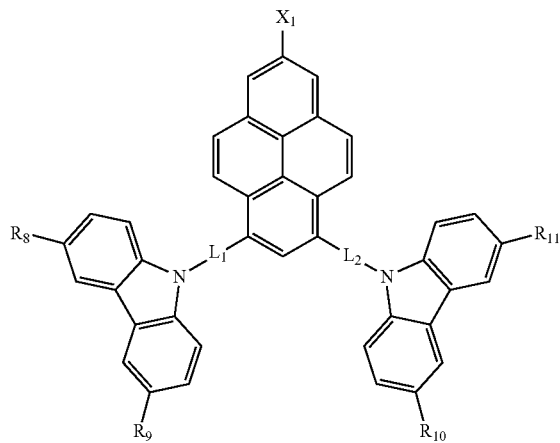

wherein, in Formula 3, $X_1$, $L_1$, $L_2$, and $R_8$ to $R_{11}$ are the same as defined in Formula 1, In Formula 3, $L_1$ and $L_2$ may be the same, $R_8$ and $R_{11}$ may be the same, and $R_9$ and $R_{10}$ may be the same.

The polycyclic compound represented by Formula 3 may be represented by the following Formula 4:

[Formula 4]

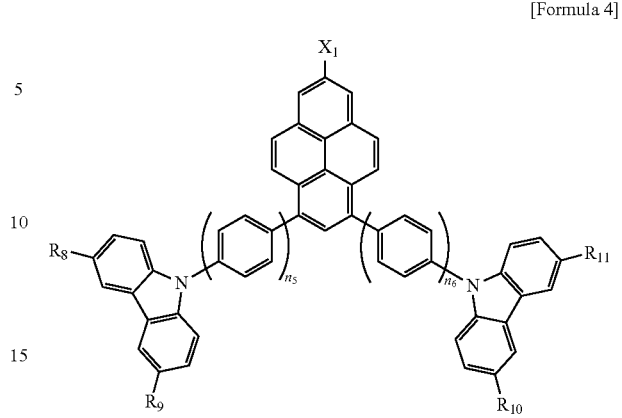

wherein, in Formula 4, "$n_5$" and "$n_6$" are each independently 1 or 2, and $X_1$, and $R_8$ to $R_{11}$ are the same as defined in Formula 1.

$R_8$ to $R_{11}$ may each be independently a halogen atom, a substituted or unsubstituted methyl group, or a substituted or unsubstituted phenyl group.

$L_1$ and $L_2$ may be each independently a substituted or unsubstituted phenylene group, or a substituted or unsubstituted divalent biphenyl group.

$X_1$ may be a substituted or unsubstituted methyl group, a substituted or unsubstituted t-butyl group, a substituted or unsubstituted dodecyl group, a substituted or unsubstituted trimethylsilyl group, or a substituted or unsubstituted triphenylsilyl group.

The polycyclic compound represented by Formula 1 may be one selected from compounds represented in the following Compound Group 1:

[Compound Group 1]

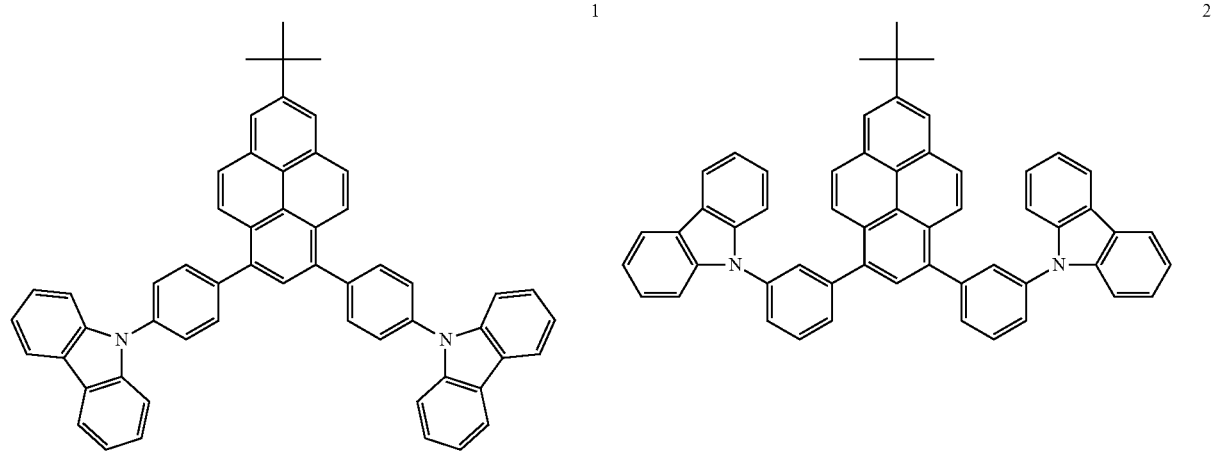

-continued
3
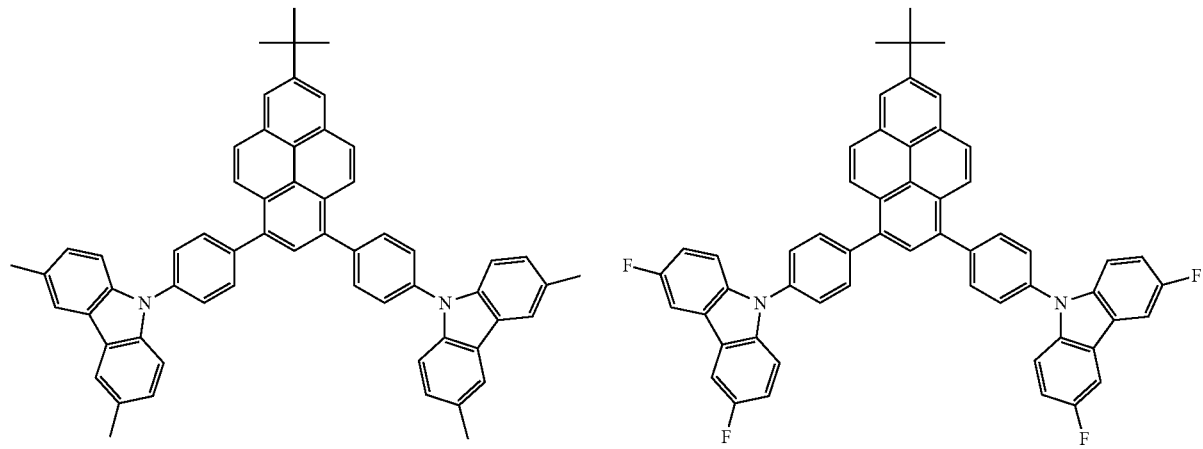
4
5
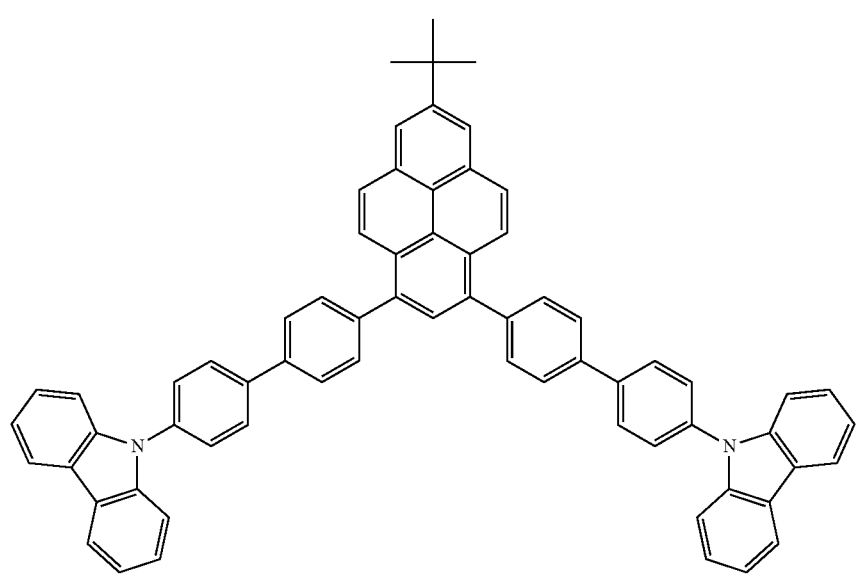
6
7
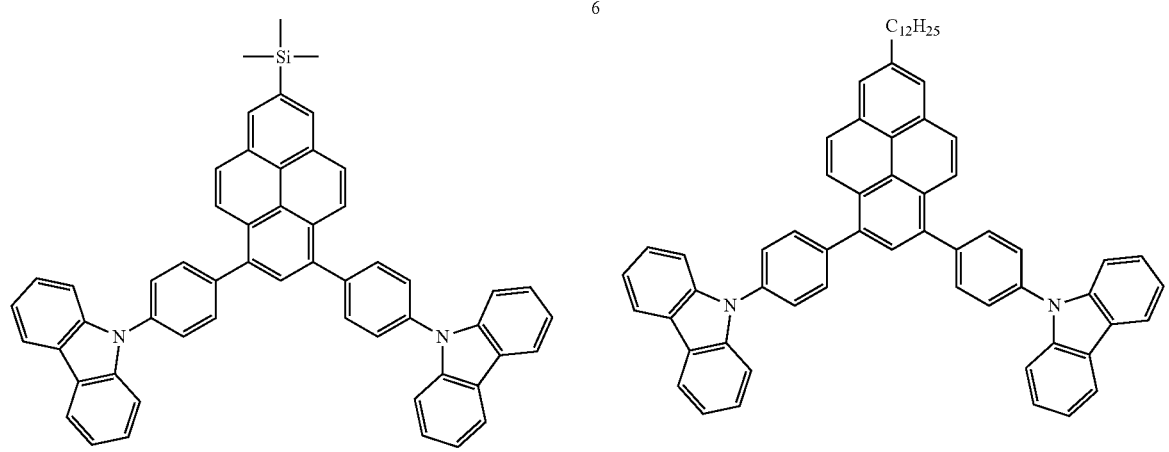

-continued
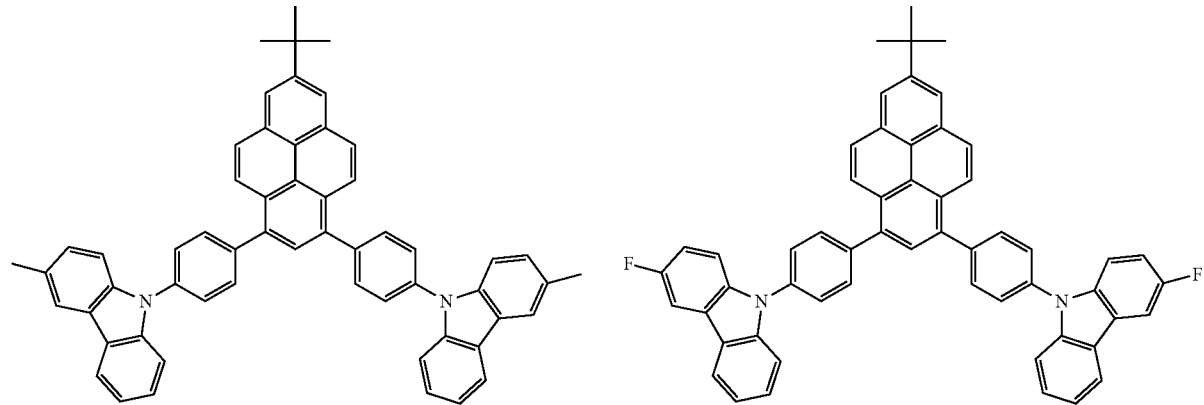
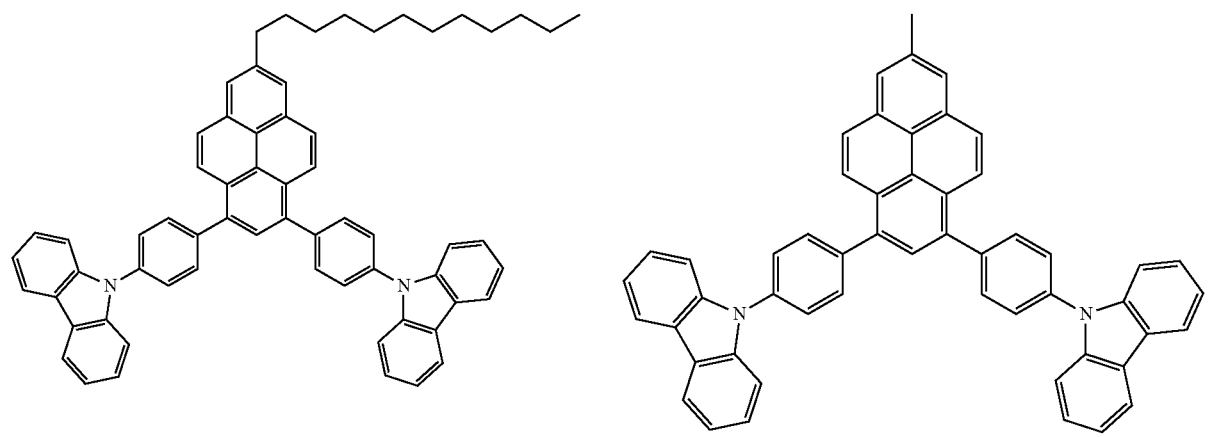
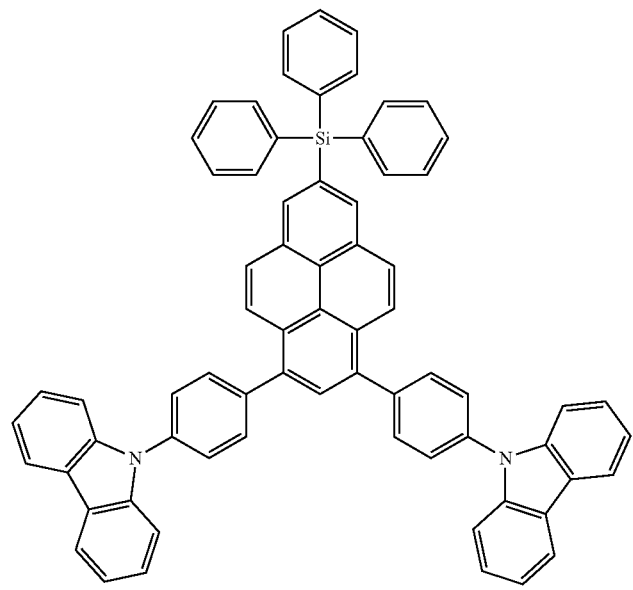

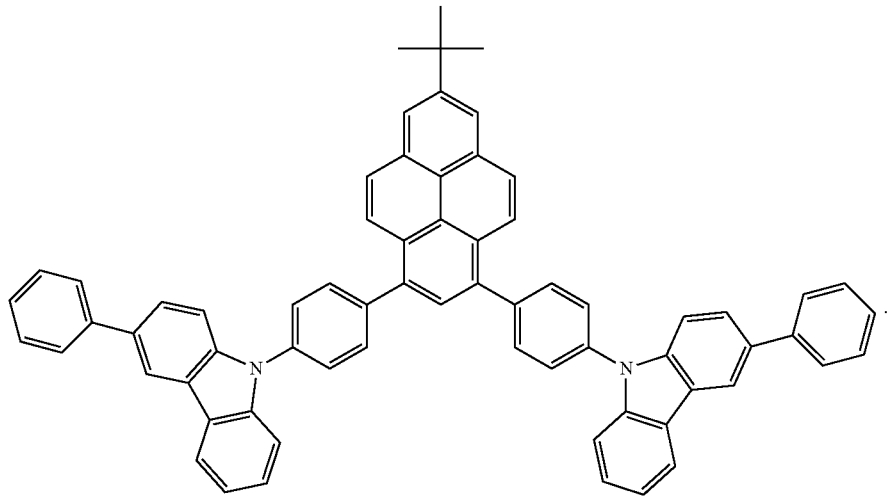

13

Embodiments are also directed to a polycyclic compound represented by the following Formula 5:

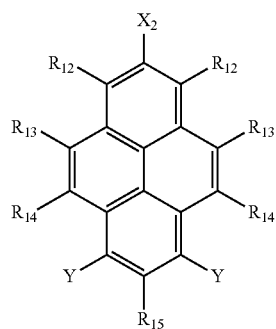

[Formula 5]

wherein in Formula 5, $X_2$ is a substituted or unsubstituted alkyl group having 1 to 12 carbon atoms, or a substituted or unsubstituted silyl group, $R_{12}$ to $R_{15}$ are each independently a hydrogen atom, a deuterium atom, a halogen atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, and Y is represented by the following Formula 6:

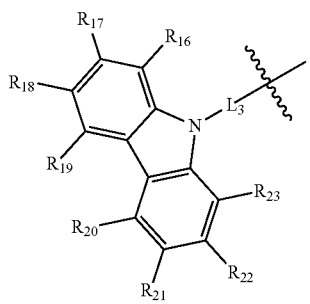

[Formula 6]

wherein, in Formula 6, $L_3$ is a substituted or unsubstituted arylene group having 6 to 30 ring carbon atoms, $R_{16}$ to $R_{23}$ are each independently a hydrogen atom, a deuterium atom, a halogen atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms.

Embodiments are also direct to an organic electroluminescence device, including a first electrode, a hole transport region on the first electrode, an emission layer on the hole transport region, an electron transport region on the emission layer, and a second electrode on the electron transport region. The emission layer may include a polycyclic compound represented by the following Formula 1:

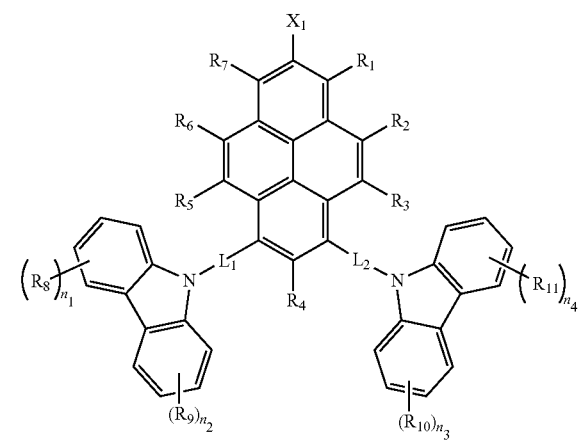

[Formula 1]

wherein in Formula 1, $X_1$ is a substituted or unsubstituted alkyl group having 1 to 12 carbon atoms, or a substituted or unsubstituted silyl group, $R_1$ to $R_{11}$ are each independently a hydrogen atom, a deuterium atom, a halogen atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, $L_1$ and $L_2$ are each independently a substituted or unsubstituted arylene group having 6 to 30 ring carbon atoms, and "$n_1$" to "$n_4$" are each independently an integer of 0 to 4.

The emission layer may include a host and a dopant. The dopant may include the polycyclic compound represented by Formula 1.

A lowest triplet excitation energy level of the host may be about 3 eV or more. The lowest triplet excitation energy level of the host may be higher than a lowest singlet excitation energy level of the dopant.

The polycyclic compound may generate reverse intersystem crossing (RISC) from a high triplet excitation energy level higher than the lowest triplet excitation energy level to a singlet excitation energy level.

A maximum emission wavelength of the emission layer may be about 480 nm or less.

The polycyclic compound represented by Formula 1 may be represented by the following Formula 2:

[Formula 2]

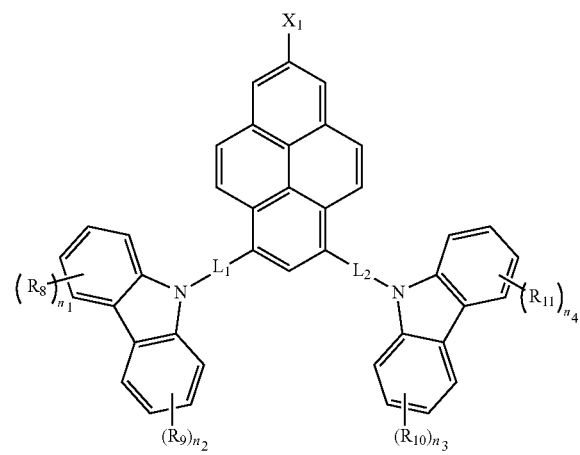

wherein, in Formula 2, $X_1$, $L_1$, $L_2$, $R_8$ to $R_{11}$, and "$n_1$" to "$n_4$" are the same as defined in Formula 1.

The polycyclic compound represented by Formula 2 may be represented by the following Formula 3:

[Formula 3]

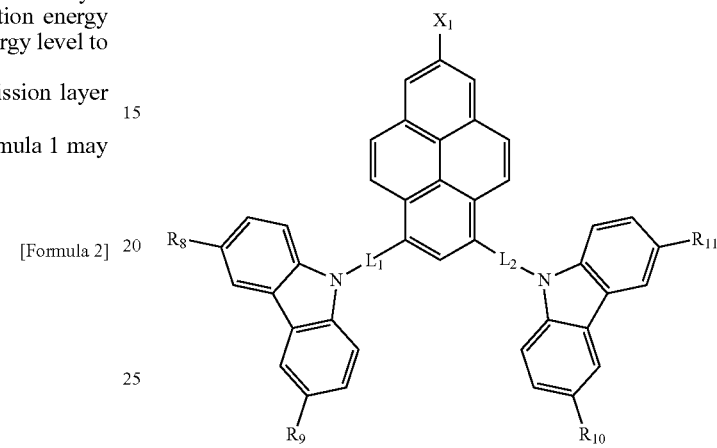

wherein, in Formula 3, $X_1$, $L_1$, $L_2$, and $R_8$ to $R_{11}$ are the same as defined in Formula 1.

$L_1$ and $L_2$ may be the same, $R_8$ and $R_{11}$ may be the same, and $R_9$ and $R_{10}$ may be the same.

The polycyclic compound represented by Formula 3 may be represented by the following Formula 4:

[Formula 4]

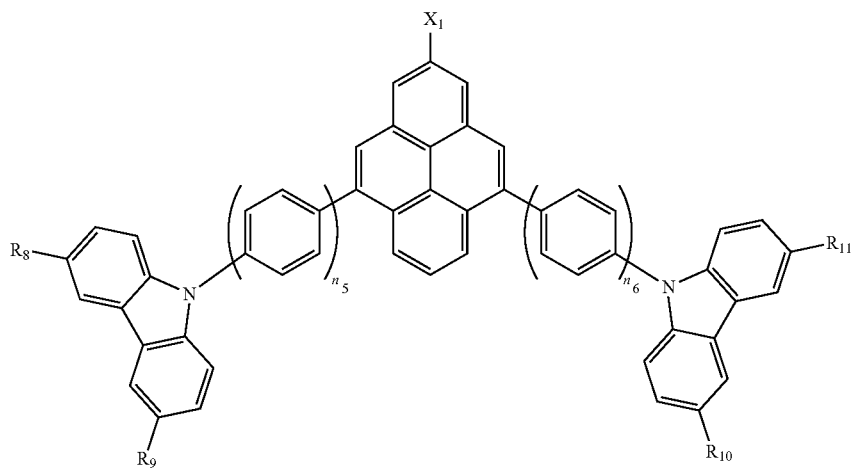

wherein, in Formula 4, "$n_5$" and "$n_6$" are each independently 1 or 2, and $X_1$, and $R_8$ to $R_{11}$ are the same as defined in Formula 1.

$R_8$ to $R_{11}$ may each independently be a halogen atom, a substituted or unsubstituted methyl group, or a substituted or unsubstituted phenyl group.

$L_1$ and $L_2$ may each independently be a substituted or unsubstituted phenylene group, or a substituted or unsubstituted divalent biphenyl group.

$X_1$ may be a substituted or unsubstituted methyl group, a substituted or unsubstituted t-butyl group, a substituted or unsubstituted dodecyl group, a substituted or unsubstituted trimethylsilyl group, or a substituted or unsubstituted triphenylsilyl group.

The polycyclic compound represented by Formula 1 may be one selected from compounds represented in the following Compound Group 1:

[Compound Group 1]

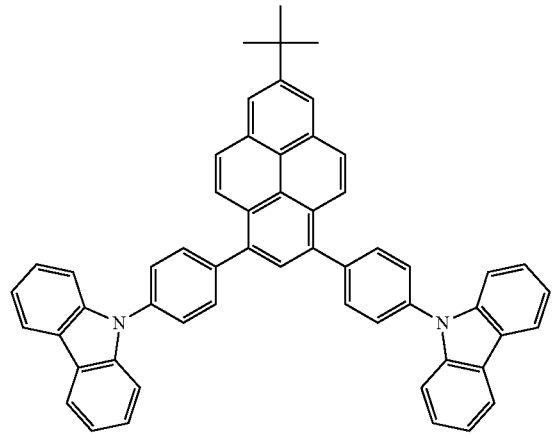

1

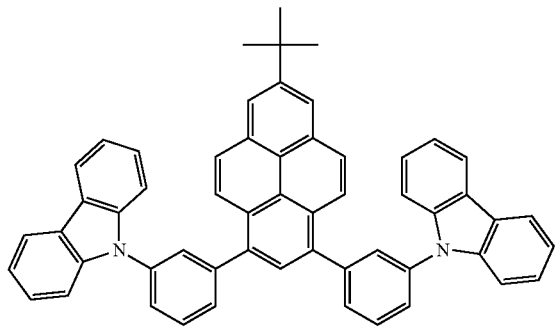

2

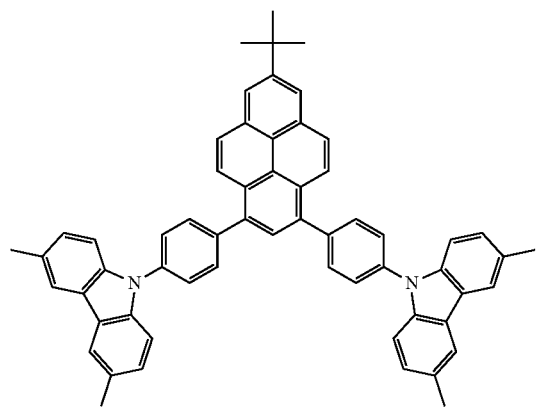

3

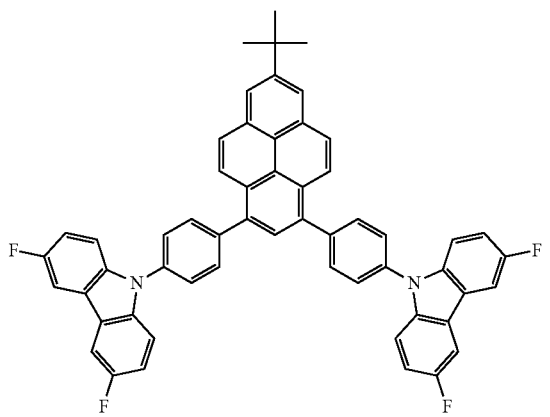

4

5
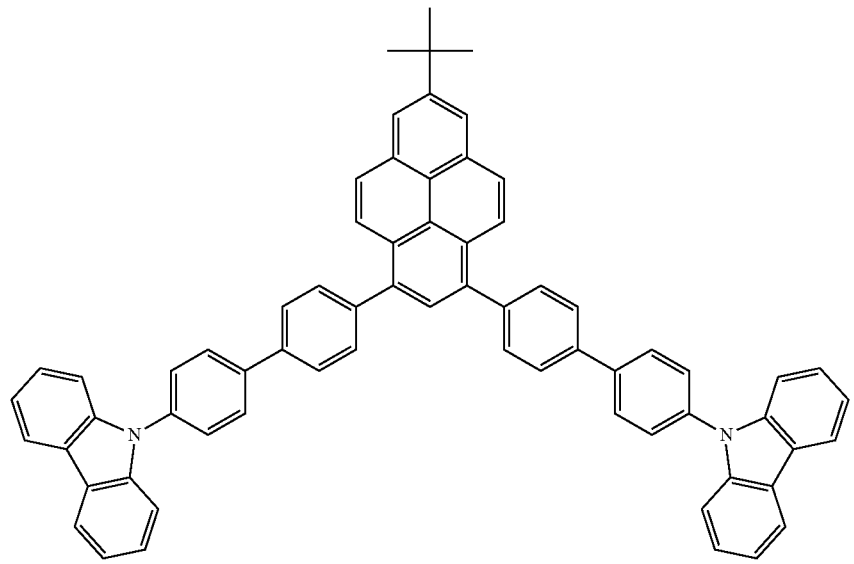
6 7
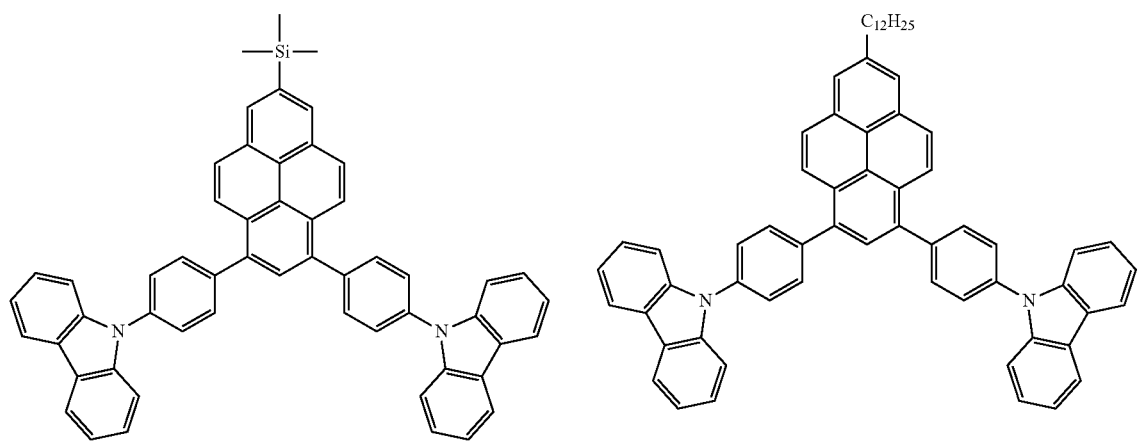
8 9
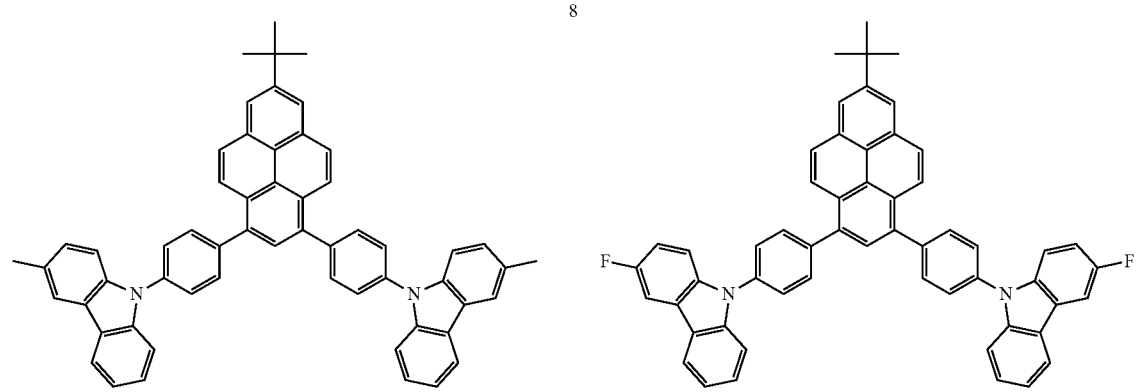

-continued
10
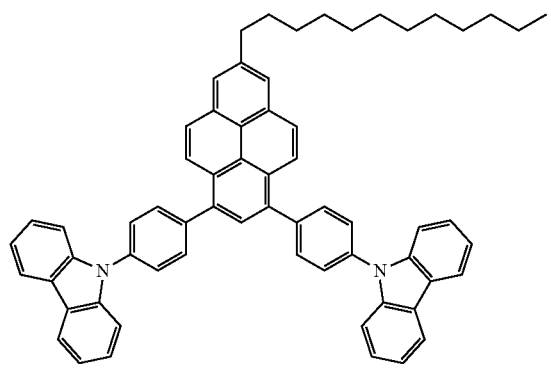
11
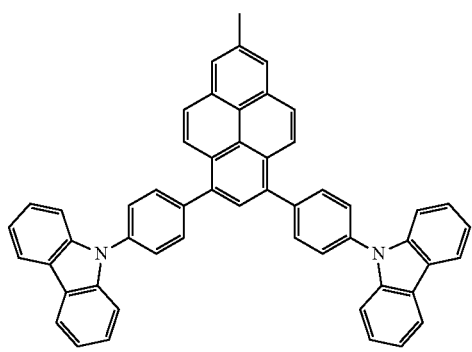
12
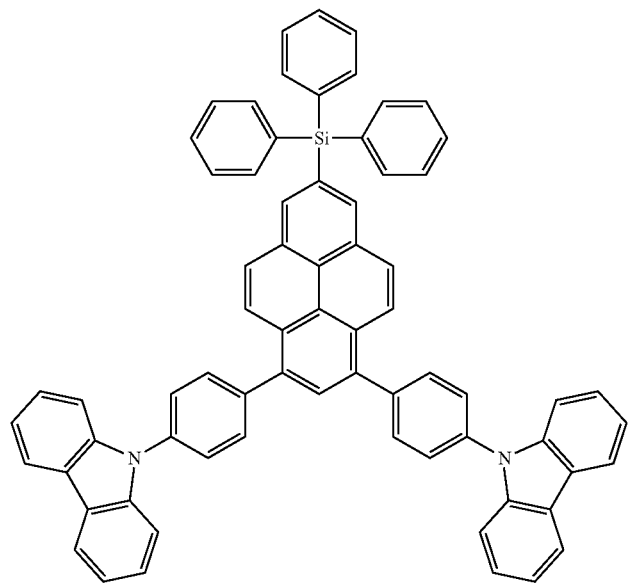
13
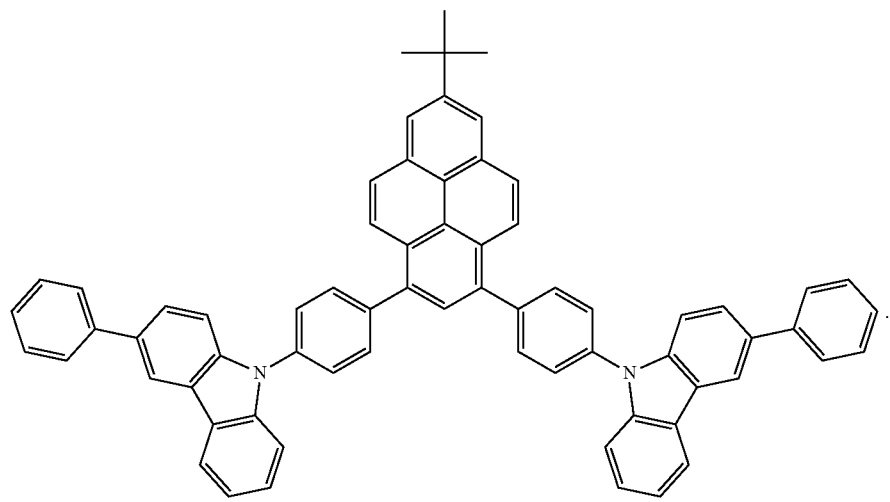

BRIEF DESCRIPTION OF THE DRAWINGS

Features will become apparent to those of skill in the art by describing in detail exemplary embodiments with reference to the attached drawings in which.

DETAILED DESCRIPTION

Figure 1:
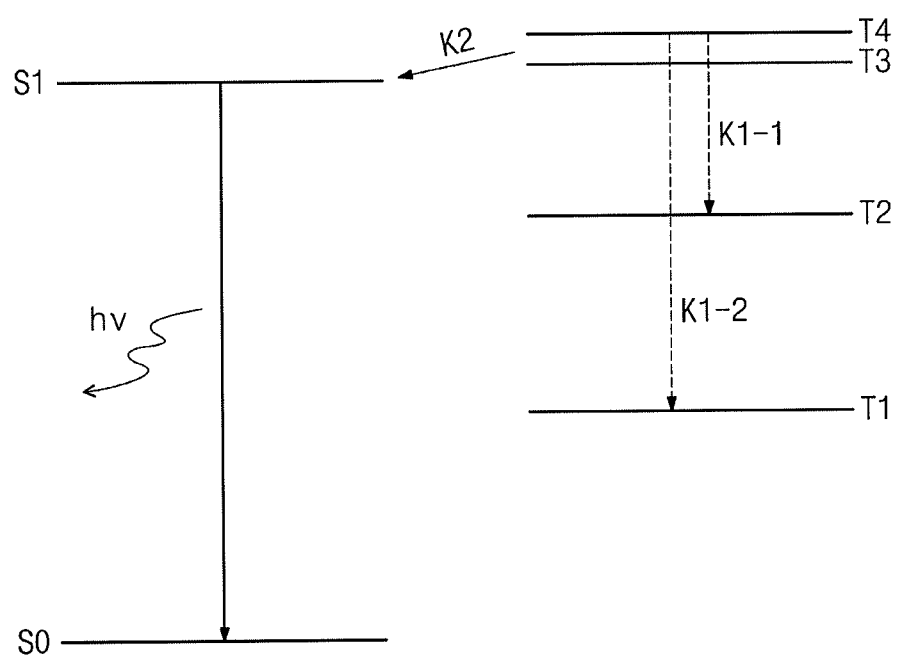
FIG. 1 illustrates an energy diagram of an excited state of a polycyclic compound according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

In the description,

in a reproduced portion of a formula represents a connection to a remaining portion of the formula.

In the description, "substituted or unsubstituted" may refer to substituted with at least one substituent selected from a deuterium atom, a halogen group, a cyano group, a nitro group, an amino group, a silyl group, an oxy group, a thio group, a sulfinyl group, a sulfonyl group, a carbonyl group, a boron group, an aryl amine group, a phosphine oxide group, a phosphine sulfide group, an alkyl group, an alkenyl group, an aryl group, and a heterocycle, or unsubstituted. Each of the substituents illustrated above may be substituted or unsubstituted. For example, a biphenyl group may be interpreted as an aryl group or a phenyl group substituted with a phenyl group.

In the description, the term "forming a ring via the combination with an adjacent group" may refer to forming a substituted or unsubstituted hydrocarbon ring, or substituted or unsubstituted heterocycle via the combination with an adjacent group. The hydrocarbon ring includes an aliphatic hydrocarbon ring and an aromatic hydrocarbon ring. The heterocycle includes an aliphatic heterocycle and an aromatic heterocycle. The hydrocarbon ring and the heterocycle may be monocyclic or polycyclic. In addition, the ring formed via the combination with an adjacent group may be combined with another ring to form a spiro structure.

In the description, the term "an adjacent group" may refer to a substituent substituted for an atom that is directly combined with an atom substituted with a corresponding substituent, another substituent substituted for an atom that is substituted with a corresponding substituent, or a substituent sterically positioned at the nearest position to a corresponding substituent. For example, in 1,2-dimethylbenzene, two methyl groups may be interpreted as "adjacent groups" to each other, and in 1,1-diethylcyclopentene, two ethyl groups may be interpreted as "adjacent groups" to each other.

In the description, the term "direct linkage" may refer to a single bond.

In the description, examples of the halogen atom may include a fluorine atom, a chlorine atom, a bromine atom and an iodine atom.

In the description, an alkyl group may be a linear, branched or cyclic type group. The carbon number of the alkyl group may be 1 to 30, 1 to 20, 1 to 15, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl. n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tctradecyl, c-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., groups.

In the description, the term "aryl" refers to an optional functional group or substituent derived from an aromatic hydrocarbon ring. The aryl group may be a monocyclic aryl group or a polycyclic aryl group. The ring carbon number in the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, biphenylene, triphenylene, pyrenyl, benzofluoranthenyl, chrysenyl, etc., groups.

In the description, the fluorenyl group may be substituted. Two substituents may be combined with each other to form a spiro structure. For example, the fluorenyl group may be a 9,9'-spirobifluorenyl group.

In the description, the term "heteroaryl" may refer to a heteroaryl group including at least one of O, N, P, S, Si or Ge as a heteroatom. The heteroaryl group may be monocyclic heteroaryl group or a polycyclic heteroaryl group. The ring carbon number may be 2 to 30, or 2 to 20. Examples of the heteroaryl group may include thiophenyl, furanyl, pyrrolyl, imidazolyl, thiazolyl, oxazolyl, oxadiazolyl, triazolyl, pyridyl, bipyridyl, pyrimidyl, triazinyl, triazolyl, acridyl, pyridazinyl, pyrazinyl, quinolinyl, quinazolinyl, quinoxalinyl, phenoxazyl, phthalazinyl, pyrido pyrimidyl, pyrido pyrazinyl, pyrazino pyrazinyl, isoquinolinyl, indolyl, carbazolyl, N-arylcarbazolyl, N-heteroarylcarbazolyl, N-alkylcarbazolyl, benzoxazolyl, benzoimidazolyl, benzothiazolyl, benzocarbazolyl, benzothiophenyl, dibenzothiophenyl, thienothiophenyl, benzofuranyl, phenanthrolinyl, thiazolyl, isooxazolyl, oxadiazolyl, thiadiazolyl, benzothiazolyl, phenothiazinyl, dibenzosilolyl, dibenzofuranyl, etc., groups.

In the description, the definition of the aryl group may be applicable to the arylene group except that the arylene group is a divalent group. The definition of the heteroaryl group may be applicable to the heteroarylene group except that the arylene group is a divalent group.

In the description, the term "silyl group" may refer to an alkyl silyl group or an aryl silyl group. Examples of the silyl group may include trimethylsilyl, triethylsilyl, t-butyldimethylsilyl, vinyldimethylsilyl, propyldimethylsilyl, triphenylsilyl, diphenylsilyl, phenylsilyl, etc., groups.

In the description, the carbon number of the amino group may be, for example, 1 to 30. The amino group may include an alkyl amino group and an aryl amino group. Examples of the amino group may include a methylamino group, a dimethylamino group, a phenylamino group, a diphenylamino group, a naphthylamino group, a 9-methyl-anthracenylamino group, a triphenylamino group, etc.

In the description, the carbon number of the carbonyl group i may be, for example, 1 to 40, 1 to 30, or 1 to 20. For example, the structures below may be included.

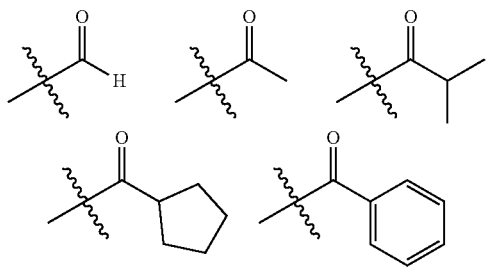

In the description, the carbon number of the sulfinyl group and the sulfonyl group may be, for example, 1 to 30. The sulfinyl group may include an alkyl sulfinyl group and an aryl sulfinyl group. The sulfonyl group may include an alkyl sulfonyl group and an aryl sulfonyl group.

In the description, the term "thio group" may include an alkylthio group and an arylthio group.

In the description, the term "oxy group" may include an alkoxy group and an aryloxy group. The alkoxy group may be a linear, branched or cyclic chain. The carbon number of the alkoxy group may be, for example, 1 to 20, or 1 to 10. Examples of the oxy group may include methoxy, ethoxy, n-propoxy, isopropoxy, butoxy, pentyloxy, hexyloxy, octyloxy, nonyloxy, decyloxy, benzyloxy, etc.

In the description, the term "boron group" may include an alkyl boron group and an aryl boron group. Examples of the boron group include trimethylboron, triethylboron, t-butyldimethylboron, triphenylboron, diphenylboron, phenylboron, etc.

In the description, an alkenyl group may be a linear chain or a branched chain. The carbon number may be, for example, 2 to 30, 2 to 20, or 2 to 10. Examples of the alkenyl group may include include vinyl, 1-butenyl, 1-pentenyl, 1,3-butadienyl aryl, styrenyl, styrylvinyl, etc. In the description, the carbon number of an amine group may be, for example, 1 to 30. The term "amine group" may include an alkylamine group and an arylamine group. Examples of the amine group may include, for example, methylamine, dimethylamine, phenylamine, diphenylamine, naphthylamine, 9-methyl-anthracenylamine, triphenylamine, etc.

In the description, the alkyl in alkylthio, alkylsulfoxy, alkylaryl, alkylamino, alkylboron, alkylsilyl, and alkylamine may be the same as the above-described examples of alkyl groups.

In the description, the aryl in aryloxy, arylthio, arylsulfoxy, acylamino, arylboron, arylsilyl and arylamine may be the same as the above-described examples of aryl groups.

Hereinafter, the polycyclic compound according to an embodiment will be explained.

The polycyclic compound according to an embodiment is represented by the following Formula 1:

[Formula 1]

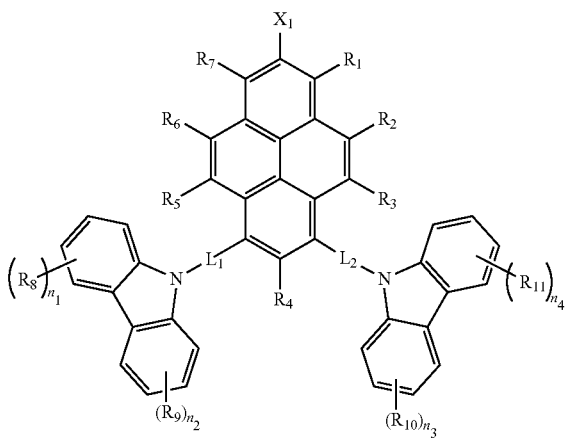

In Formula 1, $X_1$ is a substituted or unsubstituted alkyl group having 1 to 12 carbon atoms, or a substituted or unsubstituted silyl group. $X_1$ may be a substituted or unsubstituted methyl group, a substituted or unsubstituted t-butyl group, a substituted or unsubstituted dodecyl group, a substituted or unsubstituted trimethylsilyl group, or a substituted or unsubstituted triphenylsilyl group. $X_1$ may be, for example, an unsubstituted t-butyl group.

$R_1$ to $R_{11}$ are each independently a hydrogen atom, a deuterium atom, a halogen atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms. For example, $R_1$ to $R_{11}$ may each independently be a hydrogen atom, a halogen atom, a substituted or unsubstituted methyl group, or a substituted or unsubstituted phenyl group. For example, all of $R_1$ to $R_7$ may be hydrogen atoms. $R_8$ to $R_{11}$ may each independently be, for example, a halogen atom, a substituted or unsubstituted methyl group, or a substituted or unsubstituted phenyl group.

"$n_1$" to "$n_4$" are each independently an integer of 0 to 4. If "$n_1$" is 0, the polycyclic compound represented by Formula 1 may be a polycyclic compound that is unsubstituted with $R_8$. Herein, it is to be understood that when a substitution site of the compound is unsubstituted with $R_8$ to $R_{11}$, for example, when one or more of $n_1$ to $n_4$ is less than 4, a hydrogen atom may be bound to a substitution site. If "$n_1$" is an integer of 2 or more, a plurality of $R_8$ groups may be the same or different. If "$n_2$" is 0, the polycyclic compound represented by Formula 1 may be a polycyclic compound that is unsubstituted with $R_9$. If "$n_2$" is an integer of 2 or more, a plurality of R9 groups may be the same or different. If "$n_3$" is 0. the polycyclic compound represented by Formula 1 may be a polycyclic compound that is unsubstituted with $R_{10}$. If "$n_3$" is an integer of 2 or more, a plurality of $R_{10}$ groups may be the same or different. If "$n_4$" is 0, the polycyclic compound represented by Formula 1 may be a polycyclic compound that is unsubstituted with $R_{11}$. If "$n_4$" is an integer of 2 or more, a plurality of $R_{11}$ groups may be the same or different.

$L_1$ and $L_2$ are each independently a substituted or unsubstituted arylene group having 6 to 30 ring carbon atoms. $L_1$ and $L_2$ may be each independently a substituted or unsubstituted phenylene group, or a substituted or unsubstituted divalent biphenyl group. $L_1$ and $L_2$ may be each independently an unsubstituted phenylene group, or an unsubstituted divalent biphenyl group.

The polycyclic compound represented by Formula 1 may be represented by the following Formula 2:

[Formula 2]

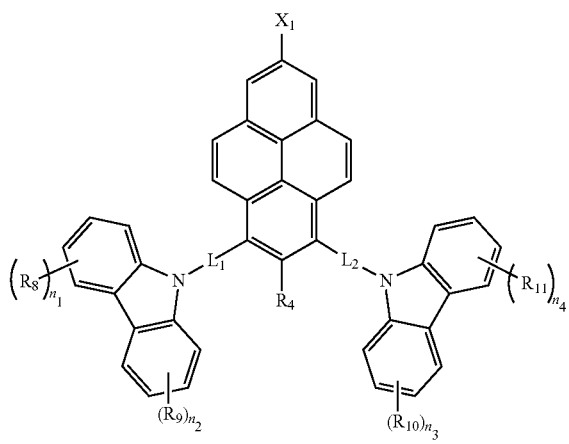

In Formula 2, $X_1$, $L_1$, $L_2$, $R_8$ to $R_{11}$, and "$n_1$" to "$n_4$" are the same as the definition in the explanation on Formula 1.

When the polycyclic compound according to an embodiment is represented by Formula 2, all $R_1$ to $R_7$ in Formula 1 may correspond to hydrogen atoms. For example, in the polycyclic compound according to an embodiment, a carbon position 2 of a pyrene core may be substituted with $X_1$, carbon positions 6 and 8 may be substituted with carbazolyl groups via linkers, and other carbon positions may be unsubstituted.

The polycyclic compound represented by Formula 2 may be represented by the following Formula 3:

[Formula 3]

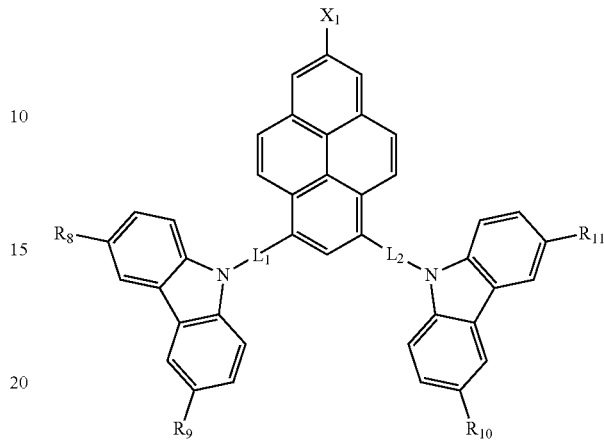

In Formula 3, $X_1$, $L_1$, $L_2$, and $R_8$ to $R_{11}$ are the same as the definition in Formula 1.

When the polycyclic compound according to an embodiment is represented by Formula 3, this polycyclic compound may correspond to Formula 2 where all "$n_1$" to "$n_4$" are 1, and $R_8$ to $R_{11}$ are substituted at carbon positions 3 and 6 of the carbazolyl groups. For example, this polycyclic compound may be a polycyclic compound according to an embodiment wherein substituents are substituted only at carbon positions 3 and 6 of carbazolyl groups and are unsubstituted at other positions.

In the polycyclic compound according to an embodiment, $L_1$ and $L_2$ may be the same, $R_8$ and $R_{11}$ may be the same, and $R_9$ and $R_{10}$ may be the same. For example, both $L_1$ and $L_2$ may be unsubstituted phenylene groups. For example, both $L_1$ and $L_2$ may be unsubstituted divalent biphenyl groups. All $R_8$ to $R_{11}$ may be halogen atoms, or unsubstituted methyl groups. Both $R_9$ and $R_{10}$ may be halogen atoms, or unsubstituted methyl groups. In the polycyclic compound according to an embodiment, when $L_1$ and $L_2$ are the same, $R_8$ and $R_{11}$ are the same, and $R_9$ and $R_{10}$ are the same, the polycyclic compound may have a symmetric structure with a pyrene core as the center.

The polycyclic compound represented by Formula 3 may be represented by the following Formula 4:

[Formula 4]

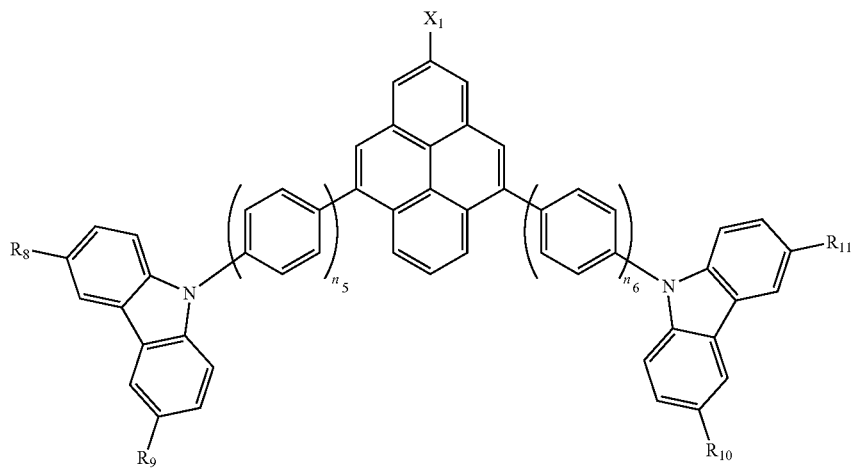

In Formula 4, $X_1$, and $R_8$ to $R_{11}$ are the same as defined in Formula 1.

"$n_5$" and "$n_6$" may be each independently 1 or 2. If "$n_5$" is 1, Formula 4 corresponds to Formula 3 where $L_1$ is an unsubstituted phenylene group. If "$n_5$" is 2, Formula 4 corresponds to Formula 3 where $L_1$ is a divalent unsubstituted biphenyl group. If "$n_6$" is 1, Formula 4 corresponds to Formula 3 where $L_2$ is an unsubstituted phenylene group. If "$n_6$" is 2, Formula 4 corresponds to Formula 3 where $L_2$ is a divalent unsubstituted biphenyl group. "$n_5$" and "$n_6$" may be the same. For example, if "$n_5$" is 1, "$n_6$" may also be 1, and if "$n_5$" is 2, "$n_6$" may also be 2.

If the polycyclic compound according to an embodiment is represented by Formula 4, the polycyclic compound may include a phenylene group or a divalent biphenyl group having a para position bonding relationship, as linkers for connecting a pyrene core and carbazolyl groups. For example, in the polycyclic compound according to an embodiment, a pyrene core and a carbazolyl group are connected at para positions of a phenylene group or a divalent biphenyl group, respectively. In addition, if "$n_5$" and "$n_6$" are the same, the polycyclic compound according to an embodiment may have the same linker for connecting a pyrene core and carbazolyl groups, where the pyrene core and the carbazolyl groups are connected via the same connection positions.

A polycyclic compound according to an embodiment may be represented by the following Formula 5:

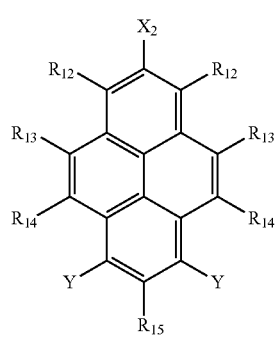

[Formula 5]

In Formula 5, $X_2$ is a substituted or unsubstituted alkyl group having 1 to 12 carbon atoms, or a substituted or unsubstituted silyl group. $X_2$ may be a substituted or unsubstituted methyl group, a substituted or unsubstituted t-butyl group, a substituted or unsubstituted dodecyl group, a substituted or unsubstituted trimethylsilyl group, or a substituted or unsubstituted triphenylsilyl group. $X_2$ may be, for example, an unsubstituted t-butyl group.

$R_{12}$ to $R_{15}$ are each independently a hydrogen atom, a deuterium atom, a halogen atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms. $R_{12}$ to $R_{15}$ may each independently be a hydrogen atom, a halogen atom, a substituted or unsubstituted methyl group, or a substituted or unsubstituted phenyl group. All $R_{12}$ to $R_{15}$ may be hydrogen atoms.

In Formula 5, Y is represented by the following Formula 6:

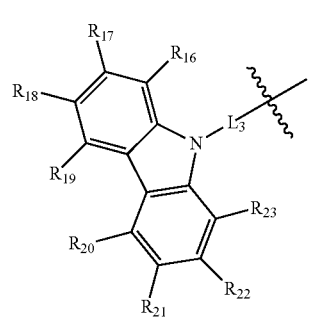

[Formula 6]

In Formula 6, $L_3$ is a substituted or unsubstituted arylene group having 6 to 30 ring carbon atoms. $L_3$ may be a substituted or unsubstituted phenylene group, or a substituted or unsubstituted divalent biphenyl group. $L_3$ may be a phenylene group or a divalent biphenyl group that has bonding relations at para positions.

When the polycyclic compound according to an embodiment is represented by Formula 5, the polycyclic compound according to an embodiment may have a structure in which substituents are symmetrically substituted with a pyrene core as the center. For example, in the polycyclic compound according to an embodiment, an $X_2$ substituent may be substituted at carbon position 2 and an $R_{15}$ substituent may be substituted at carbon position 7 of a pyrene core, and each substituent may be connected in a line symmetrical relationship with a line connecting a carbon of position 2 and a carbon of position 7 as the center. For example, in the polycyclic compound according to an embodiment, the same $R_{12}$ substituents may be connected at carbon position 1 and carbon position 3, the same $R_{13}$ substituents may be connected at carbon position 4 and carbon position 10, the same $R_{14}$ substituents may be connected at carbon position 5 and carbon position 9, and the same Y substituents may be connected at carbon position 6 and carbon position 8 in the pyrene core. For example, in the polycyclic compound according to an embodiment, the same carbazolyl groups may be connected via the same linker, $L_3$, with carbon at position 6 and carbon at position 8.

The polycyclic compound represented by Formula 1 may be selected from, for example, the compounds represented in Compound Group 1.

[Compound Group 1]
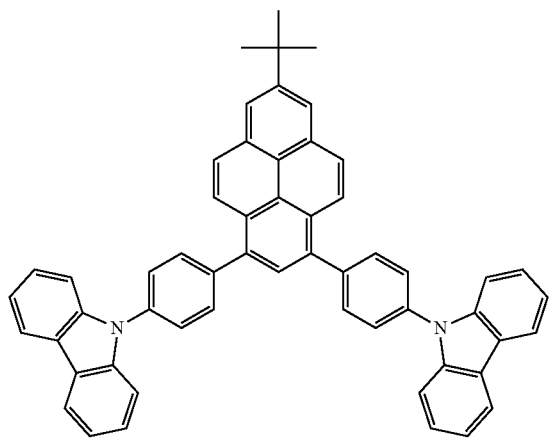
1
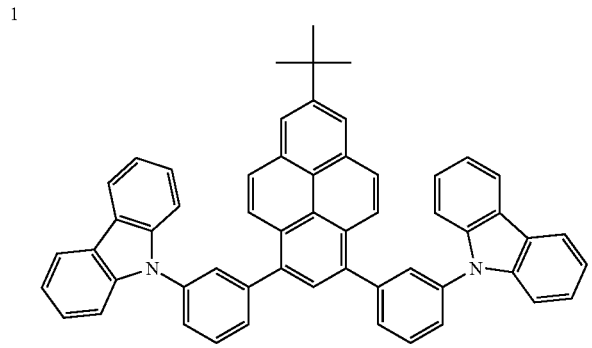
2
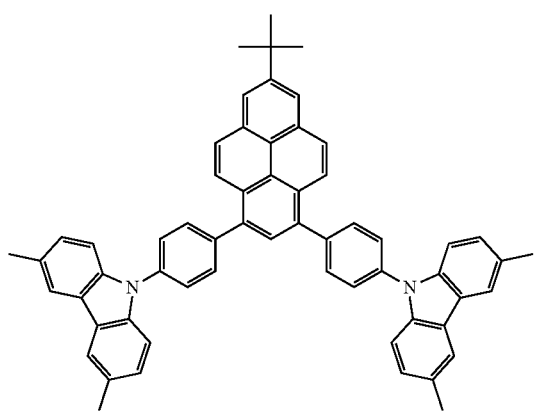
3
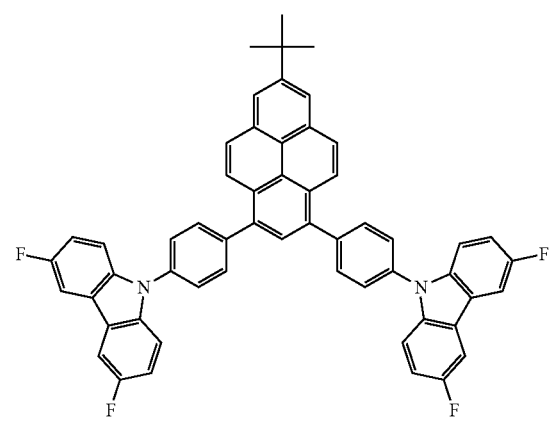
4
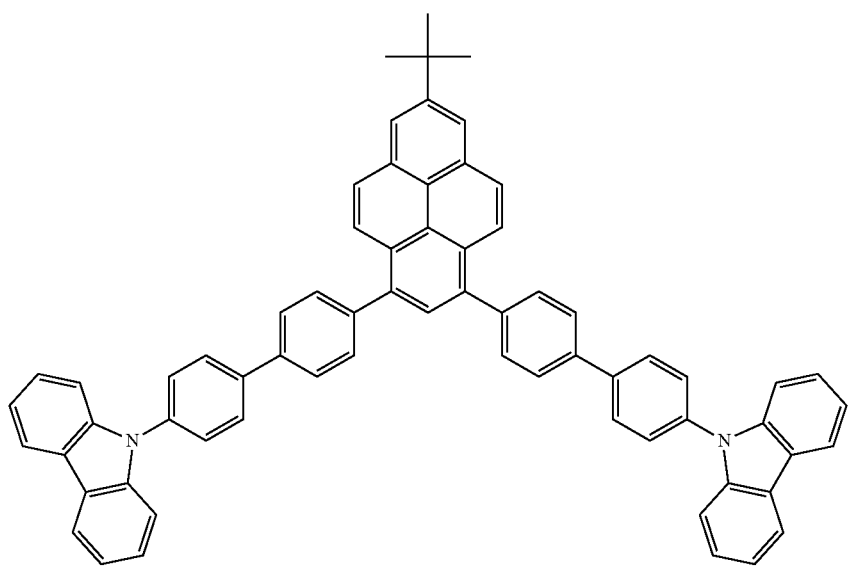
5

-continued
6
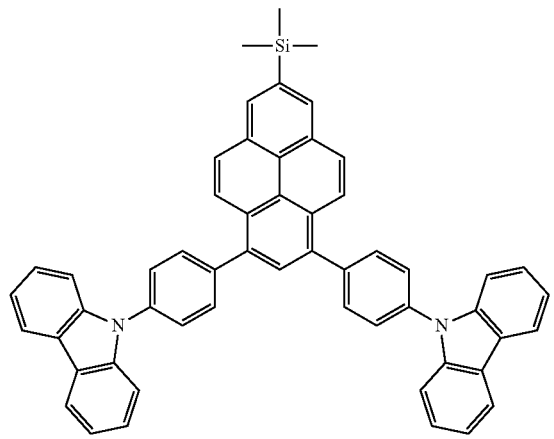
7
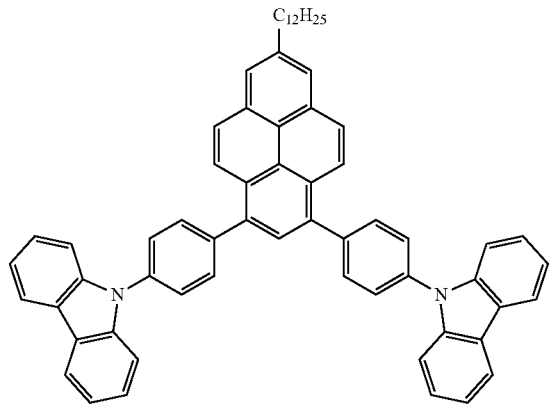
8
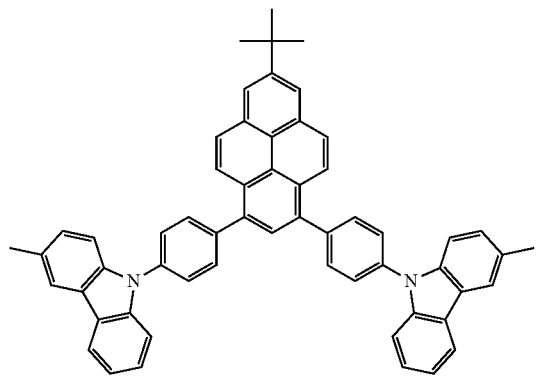
9
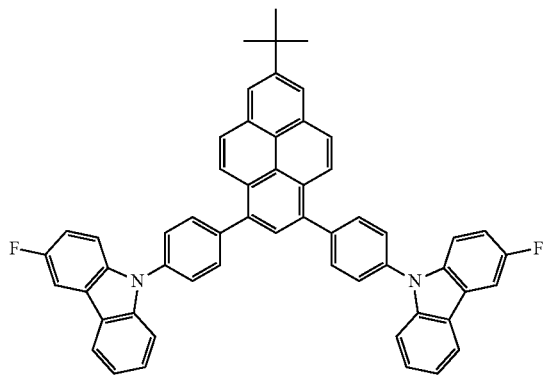
10
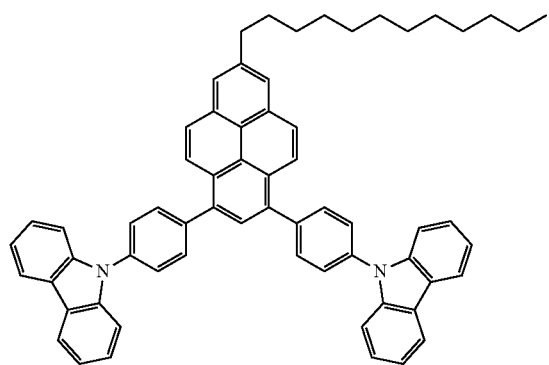
11
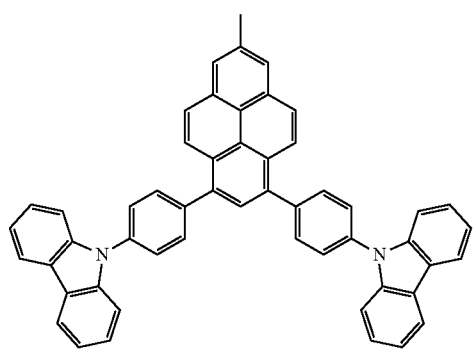

-continued

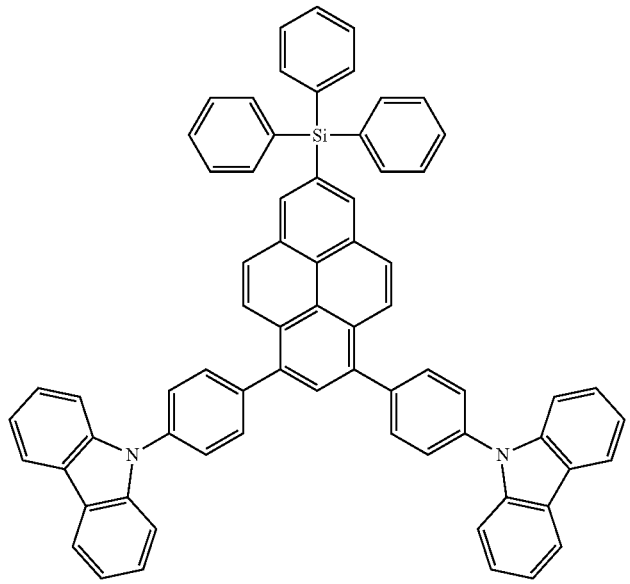

12

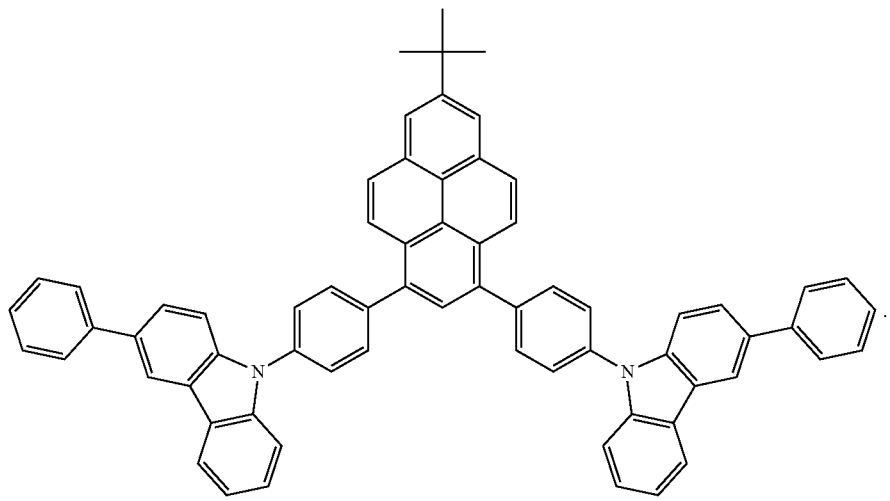

13

In the polycyclic compound according to an embodiment, two carbazolyl groups may be connected to a pyrene core via linkers. For example, the carbazolyl groups may be symmetrically connected at carbon position 6 and carbon position 8 of the pyrene core.

If the polycyclic compound represented by Formula 1 is applied to an organic electroluminescence device, reverse intersystem crossing may occur. In the description, "reverse intersystem crossing" may refer to the transition from a triplet state to a singlet state.

FIG. 1 illustrates an energy diagram of an excited state of a polycyclic compound according to an embodiment. FIG. 1 illustrates a reverse intersystem crossing (K2) of transition from the fourth triplet excitation state (T4) to the lowest singlet excitation state (S1). The term "reverse intersystem crossing (K2)" may also refer to the transition from the fifth triplet excitation state to the lowest singlet excitation state (S1), or from the fifth triplet excitation state to the second singlet excitation state. The generation of the reverse intersystem crossing is not specifically limited as long as the crossing is generated from a high triplet excitation state (Tn) to a singlet excitation state which has a close energy level value.

Referring to FIG. 1, if the polycyclic compound according to an embodiment is excited in an organic electroluminescence device, the transition (K2) of excitons from the fourth triplet excitation state (T4) to a singlet excitation state (S1) that is adjacent to the fourth triplet excitation state (T4) may happen easily. However, transitions (K1-1, K1-2) from the fourth triplet excitation state (T4) to the second triplet excitation state (T2) or the lowest triplet excitation state (T1), which are triplet excitation states having a lower energy level than the fourth triplet excitation state (T2), are unlikely to happen. In the polycyclic compound according to an embodiment, the transitions (K1-1, K1-2) from the fourth triplet excitation state (T4) which has a high triplet excitation state to a triplet excitation states (T2, T1) which have a lower energy level than the fourth triplet excitation state (T4), are restrained, and the transition (K2) to a singlet excitation state (S1) that is adjacent to the fourth triplet excitation state (T4) may be induced. Excitons transited to the singlet excitation state (S1) may transit to a ground state (S0) such that light emission (hv) may occur. For example, the polycyclic compound according to an embodiment may have a light emission mechanism based on the transition from a singlet state to a ground state. The polycyclic compound according to an embodiment may be a fluorescence emission material. The polycyclic compound according to an embodiment may be a delayed fluorescence emission material.

In the polycyclic compound represented by Formula 1, a bulky substituent having a large volume such as a t-butyl group may be substituted at carbon position 2 of a pyrene core. In addition, carbazolyl groups may be symmetrically connected at carbon positions 6 and 8 of the pyrene core. Due to the above-described structure of the polycyclic compound represented by Formula 1, the transition from a high triplet excitation state (Tn) (n is an integer of 3 or more) to a triplet excitation state having a lower energy level (Tn-1, Tn-2, Tn-3. . . etc.) may be restrained. Accordingly, the transition from a high triplet excitation state to an adjacent singlet excitation state of the polycyclic compound according to an embodiment may be induced. For example, the transition (K2) of the fourth triplet excitation state (T4) to an adjacent singlet excitation state (S1) of the polycyclic compound according to an embodiment may be induced as shown in FIG. 1.

A light emission mechanism for emitting light after the transition of triplet excitons to singlet excitons may be thermally activated delayed fluorescence (TADF). Thermally activated delayed fluorescence requires heat greater than a certain degree for the transition from the lowest triplet excitation state (T1) to a singlet excitation state (S1). Accordingly, there may be a high probability of generating a roll-off phenomenon by which luminance drops rapidly under a high current density. In addition, with thermally activated delayed fluorescence it may be difficult to provide an emission wavelength corresponding to deep blue, as compared to common fluorescence. The polycyclic compound according to an embodiment may use a triplet excitation state (for example, T3 or T4) having a higher energy level than the lowest triplet excitation state (T1). Accordingly, thermal energy required for the transition of the triplet excitons to the singlet excitons may be extremely low or zero. As a result, if the polycyclic compound according to an embodiment is applied to an organic electroluminescence device, deep blue emission with high efficiency may be accomplished, and the probability of generating the roll-off phenomenon of the organic electroluminescence device may be minimized.

Hereinafter, an organic electroluminescence device according to an embodiment will be explained. Hereinafter, different features from the above-described polycyclic compound according to an embodiment will be mainly explained in particular. and unexplained parts will follow the above explanation on the polycyclic compound according to an embodiment.

The organic electroluminescence device according to an embodiment includes the above-described polycyclic compound according to an embodiment.

Figure 2:
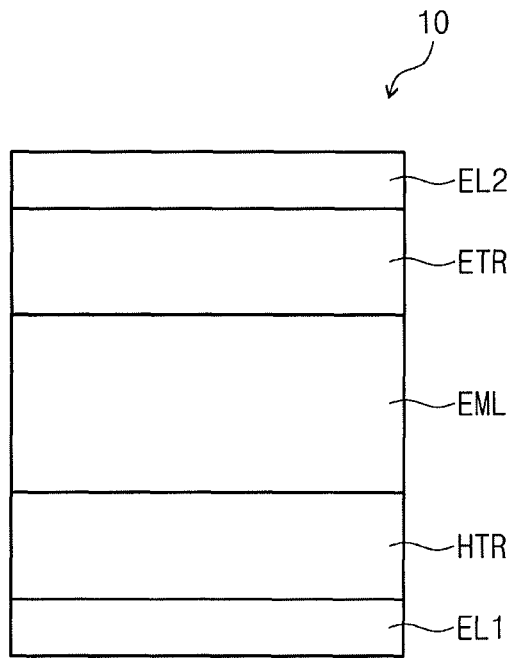
FIG. 2 illustrates a cross-sectional view schematically depicting an organic electroluminescence device according to an embodiment.
Figure 3:
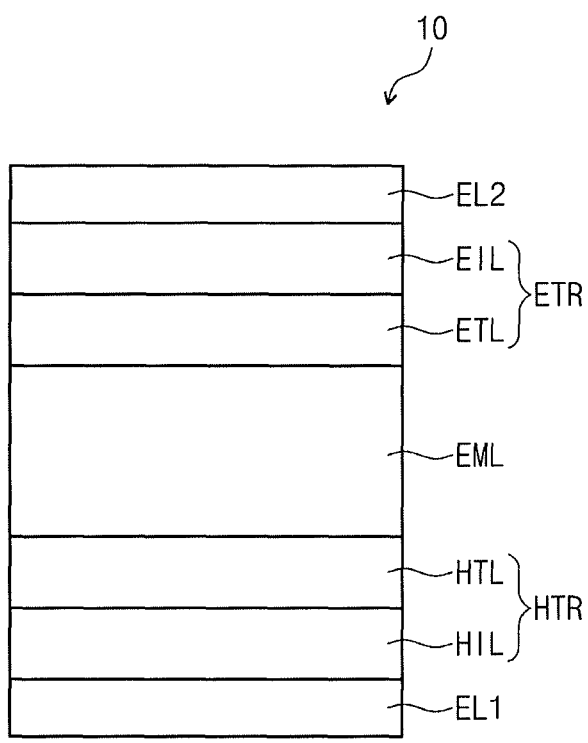
FIG. 3 illustrates a cross-sectional view schematically depicting an organic electroluminescence device according to an embodiment.

FIG. 2 illustrates a cross-sectional view schematically depicting an organic electroluminescence device according to an embodiment. FIG. 3 illustrates a cross-sectional view schematically depicting an organic electroluminescence device according to an embodiment.

Referring to FIG. 2 and FIG. 3, organic electroluminescence devices (10) according to exemplary embodiments include a first electrode EL1, a hole transport region HTR, an emission layer EML, an electron transport region ETR and a second electrode EL2.

The first electrode EL1 has conductivity. The first electrode EL1 may be a pixel electrode or an anode. The first electrode EL1 may be a transmissive electrode, a transflective electrode, or a reflective electrode. If the first electrode EL1 is a transmissive electrode, the first electrode EL1 may be formed using a transparent metal oxide such as indium tin oxide (ITO), indium zinc oxide (IZO), zinc oxide (ZnO), and indium tin zinc oxide (ITZO). If the first electrode EL1 is a transflective electrode or reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof or a mixture thereof (for example, a mixture of Ag and Mg). The first electrode EL1 may include a plurality of layers including the reflective layer or transflective layer formed using the above materials, or a transparent layer formed using ITO, IZO, ZnO, or ITZO.

A hole transport region HTR may be provided on the first electrode EL1. The hole transport region HTR may include at least one of a hole injection layer HIL, a hole transport layer HTL, a hole buffer layer, or an electron blocking layer.

The hole transport region HTR may have a single layer formed using a single material, a single layer formed using a plurality of different materials, or a multilayer structure including a plurality of layers formed using a plurality of different materials.

For example, as shown in FIG. 3, the hole transport region HTR may have a single layer of a hole injection layer HIL or a hole transport layer HTL, and may have a single layer structure formed using a hole injection material and a hole transport material. In some implementations, the hole transport region HTR may have a single layer structure formed using a plurality of different materials, or a structure laminated from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/ electron blocking layer, as examples.

The hole transport region HTR may be formed using a suitable method such as a vacuum deposition method, a spin coating method, a cast method, a Langmuir-Blodgett (LB) method, an inkjet printing method, a laser printing method or a laser induced thermal imaging (LITI) method.

The hole injection layer HIL may include, for example, a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4"-tris(3-methylphenylphenylamino) triphenylamine (m-MTDATA), 4,4', 4"-tris(N,N-diphenylamino)triphenylamine (TDATA), 4,4', 4"-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthyl)-N,N'-diphenyl-(1,1'-biphenyl)-4,4'-diamine (NPD), triphenylamine-containing polyether ketone (TPAPEK), 4-isopropyl-4'-methyldiphenyliodonium tetrakis(pentafluorophenyl)borate, 1,4,5,8,9,11-hexaazatriphenylenehexacarbonitrile (HAT-CN), etc.

The hole transport layer HTL may include, for example, carbazole derivatives such as N-phenyl carbazole, polyvinyl carbazole, and 1,3-bis(N-carbazolyl)benzene (mCP), fluorene-based derivatives, N,N'-bis(3-methylphenyl)-N,N'-diphenyl-[1,1-biphenyl]-4,4'-diamine (TPD), triphenylamine-based derivatives such as 4,4',4''-tris(N-carbazolyl) triphenylamine (TCTA), N,N'-di(1-naphthyl)-N,N'-diphenyl-(1,1'-biphenyl)-4,4'-diamine (NPD), 4,4'-cyclohexylidene bis[N,N-bis(4-methylphenyl) benzenamine] (TAPC), 4,4'-bis[N,N'-(3-tolyl)amino]-3,3'-dimethylbiphenyl (HMTPD), etc.

The thickness of the hole transport region HTR may be from about 150 Å to about 12,000 Å, for example, from about 150 Å to about 1,500 Å. If the hole transport region HTR includes both the hole injection layer HIL and the hole transport layer HTL, the thickness of the hole injection layer HIL may be from about 100 Å to about 10,000 Å, or, for example, from about 100 Å to about 1,000 Å, and the thickness of the hole transport layer HTL may be from about 50 Å to about 1,000 Å. If the thicknesses of the hole transport region HTR, the hole injection layer HIL, and the hole transport layer HTL satisfy the above-described ranges, satisfactory hole transport properties may be obtained without substantial increase of a driving voltage.

The hole transport region HTR may further include a charge generating material in addition to the above-described materials to increase conductivity. The charge generating material may be dispersed uniformly or non-uniformly in the hole transport region HTR. The charge generating material may be, for example, a p-dopant. The p-dopant may be one of a quinone derivative, a metal oxide, or a cyano group-containing compound, as examples. For example, the p-dopant may include a quinone derivative such as tetracyanoquinodimethane (TCNQ) or 2,3,5,6-tetrafluoro-7,7,8,8-tetracyanoquinodimethane (F4-TCNQ), or a metal oxide such as tungsten oxide or molybdenum oxide.

As described above, the hole transport region HTR may further include at least one of a hole buffer layer or an electron blocking layer EBL in addition to the hole injection layer HIL and the hole transport layer HTL. The hole buffer layer may compensate a resonance distance according to the wavelength of light emitted from the emission layer EML and increase light emission efficiency. Materials included in the hole transport region HTR may be used as materials included in the hole buffer layer. The electron blocking layer may be a layer that prevents electron injection from the electron transport region ETR to the hole transport region HTR.

An emission layer EML may be provided on the hole transport region HTR. The emission layer EML may be disposed on the hole transport layer HTL and may contact the hole transport layer HTL. The emission layer EML may have a thickness of, for example, from about 100 Å to about 600 Å. The emission layer EML may have a single layer formed using a single material, a single layer formed using a plurality of different materials, or a multilayer structure having a plurality of layers formed using a plurality of different materials.

Hereinafter, an embodiment of including the polycyclic compound according to an embodiment in an emission layer EML will be described. The polycyclic compound according to an embodiment may be included in at least one layer among organic layers disposed between the first electrode EL1 and the second electrode EL2.

The emission layer EML may include the polycyclic compound according to an embodiment. For example, the organic electroluminescence device according to an embodiment may include a polycyclic compound represented by Formula 1 in an emission layer EML.

[Formula 1]

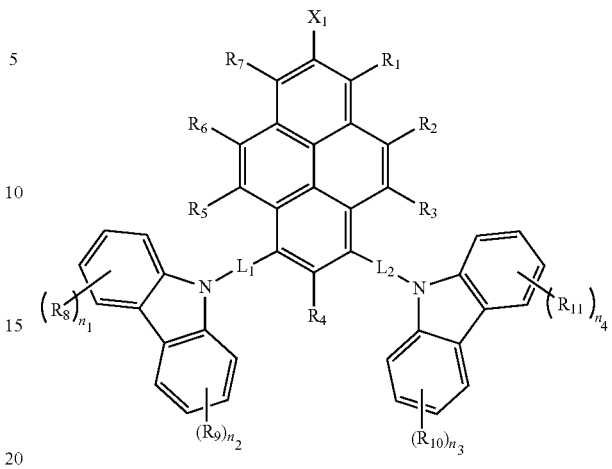

In Formula 1, $X_1$, $L_1$, $L_2$, $R_1$ to $R_{11}$ and "$n_1$" to "$n_4$" may be the same as described above.

The polycyclic compound represented by Formula 1 may be as described above, and a particular explanation thereof will not be repeated.

The emission layer EML may emit one of red light, green light, blue light, white light, yellow light, or cyan light. The emission layer EML may include a fluorescence material or a phosphorescence material. The polycyclic compound according to an embodiment may be a material that emits blue light. The polycyclic compound according to an embodiment may be a material that emits light at a wavelength of about 480 nm or less. For example, the maximum emission wavelength of the emission layer EML may be about 480 nm or less. The emission layer EML may be a blue emission layer. The emission layer EML may emit light of which maximum emission wavelength is about 480 nm or less. The emission layer EML may, for example, emit blue light in a wavelength region of about 430 nm to about 480 nm. The emission layer EML may emit deep blue light in a wavelength region of about 430 nm to about 450 nm. Herein, the term "maximum emission wavelength" refers to the wavelength having the greatest intensity.

The polycyclic compound according to an embodiment may provide a light emission mechanism based on the transition from a singlet state to a ground state. The polycyclic compound according to an embodiment may be a fluorescence emission material. An organic electroluminescence device including the polycyclic compound according to an embodiment in an emission layer EML may be a fluorescence emission device.

The emission layer EML may include a host and a dopant. The lowest triplet excitation energy level of the host included in the emission layer EML may be higher than the lowest singlet excitation energy level of the dopant. For example, the lowest triplet excitation energy level of the host included in the emission layer EML may be about 3 eV or more, and the lowest singlet excitation energy level of the dopant may be about 2.8 eV or less. In this case, a efficiency decrease due to a reverse energy movement from the dopant to the host may be minimized.

The host material of the emission layer EML may be selected from anthracene derivatives, fluoranthene derivatives, pyrene derivatives, arylacetylene derivatives, fluorene derivatives, perylene derivatives, chrysene derivatives, phenanthrene derivatives, spiro-acridine derivatives, etc. For example, pyrene derivatives, perylene derivatives, chrysene derivatives, phenanthrene derivatives, anthracene derivatives, and spiro-acridine derivatives may be used.

The host may be a suitable host material such as, for example, tris(8-hydroxyquinolino)aluminum ($Alq_3$), 4,4'-bis (N-carbazolyl)-1,1'-biphenyl (CBP), poly(N-vinylcarbazole) (PVK), 9,10-di(naphthalene-2-yl)anthracene (ADN), 4,4',4"-tris(carbazol-9-yl)-triphenylamine (TCTA), 1,3,5-tris(N-phenylbenzimidazole-2-yl)benzene (TPBi), 3-tert-butyl-9,10-di(naphth-2-yeanthracene (TBADN), distyrylarylene (DSA), 4,4'-bis(9-carbazolyl)-2,2'-dimethyl-biphenyl (CDBP), and 2-methyl-9,10-bis(naphthalen-2-yl)anthracene (MADN). The host may include 10,10'-diphenyl-10H,10'H-9,9'-spirobi[acridine].

The polycyclic compound represented by Formula 1 may be included as the dopant material of an emission layer EML.

In the organic electroluminescence device according to an embodiment, the dopant may further include another material in addition to the polycyclic compound represented by Formula 1. The dopant may include, for example, a styryl derivative (for example, 1,4-bis[2-(3-N-ethylcarbazoryl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi)), perylene or a derivative thereof (for example, 2,5,8,11-tetra-tert-butylperylene (TBP)), pyrene or a derivative thereof (for example, 1,1-dipyrene, 1,4-dipyrenylbenzene, and 1,4-bis(N,N-diphenylamino)pyrene). The dopant may be 10-phenyl-10H,10'H-spiro [acridine-9,9'-anthracen]-10'-one (ACRSA).

If the emission layer EML is to emit red light, the emission layer EML may further include a fluorescence material including, for example, tris(dibenzoylmethanato) phenanthroline europium ($PBD:Eu(DBM)_3(Phen)$) or perylene. If the emission layer EML is to emit red light, the dopant included in the emission layer EML may be selected from a metal complex or an organometallic complex such as bis(1-phenylisoquinoline)acetylacetonate iridium (PIQIr(acac)), bis(1-phenylquinoline)acetylacetonate iridium (PQIr (acac)), tris(1-phenylquinoline)iridium (PQIr), and octaethylporphyrin platinum (PtOEP), rubrene and the derivatives thereof, and 4-dicyanomethylene-2-(p-dimethylaminostyryl)-6-methyl-4H-pyrane (DCM) and the derivatives thereof.

If the emission layer EML is to emit green color, the emission layer EML may further include a fluorescence material including tris(8-hydroxyquinolino)aluminum ($Alq_3$). If the emission layer EML is to emit green light, the dopant included in the emission layer EML may be selected from a metal complex or an organometallic complex such as fac-tris(2-phenylpyridine)iridium ($Ir(ppy)_3$), and coumarin and the derivatives thereof.

If the emission layer EML is to emit blue light, the emission layer EML may further include a fluorescence material including any one selected from the group consisting of spiro-DPVBi, spiro-6P, distyryl-benzene (DSB), distyryl-arylene (DSA), a polyfluorene (PFO)-based polymer, and a poly(p-phenylene vinylene) (PPV)-based polymer. If the emission layer EML is to emit blue light, the dopant included in the emission layer EML may be selected from a metal complex or an organometallic complex such as $(4,6-F_2ppy)_2Irpic$, and perylene and the derivatives thereof.

An electron transport region ETR may be provided on the emission layer EML. The electron transport region ETR may include at least one of a hole blocking layer, an electron transport layer ETL, or an electron injection layer EIL, as examples.

The electron transport region ETR may have a single layer formed using a single material, a single layer formed using a plurality of different materials, or a multilayer structure having a plurality of layers formed using a plurality of different materials.

For example, as shown in FIG. 3, the electron transport region ETR may have a single layer structure of an electron injection layer EIL or an electron transport layer ETL, or a single layer structure formed using an electron injection material and an electron transport material. Further, the electron transport region ETR may have a single layer structure having a plurality of different materials, or a structure laminated from the first electrode EL1 of electron transport layer ETL/electron injection layer EIL, or hole blocking layer/electron transport layer ETL/electron injection layer EIL, as examples.

The electron transport region ETR may be formed using a suitable method such as a vacuum deposition method, a spin coating method, a cast method, a Langmuir-Blodgett (LB) method, an inkjet printing method, a laser printing method, or a laser induced thermal imaging (LITI) method.

The electron transport region ETR may include, for example, tris(8-hydroxyquinolinato)aluminum ($Alq_3$), 1,3, 5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate (Bebq2), 9,10-di(naphthalene-2-yl) anthracene (ADN), bis[2-(diphenylphosphino)phenyl]ether oxide (DPEPO), 3,3",5,5"-tetra(pyridine-3-yl)-1,1':3',1"-terphenyl (BmPyPhB) and a mixture thereof. The thickness of the electron transport layers ETL may be from about 100 Å to about 1,000 Å, or, for example, from about 150 Å to about 500 Å. If the thickness of the electron transport layers ETL satisfies the above-described range, satisfactory electron transport properties may be obtained without substantial increase of a driving voltage.

If the electron transport region ETR includes an electron injection layer EIL, a metal such as Al, Ag, Li, Mg and Ca, or a mixture thereof may be included. For example, the electron injection layer EIL may use LiF, lithium quinolate (LiQ), $Li_2O$, BaO, NaCl, CsF, a metal in lanthanoides such as Yb, or a metal halide such as RbCl, and RbI. The electron injection layer EIL may also be formed using a mixture material of an electron transport material and an insulating organo metal salt. The organo metal salt may be a material having an energy band gap of about 4 eV or more. The organo metal salt may include, for example, a metal acetate, a metal benzoate, a metal acetoacetate, a metal acetylacetonate, or a metal stearate. The thickness of the electron injection layer EIL may be from about 10 Å to about 100 Å. If the thickness of the electron injection layer EIL satisfies the above-described range, satisfactory electron injection properties may be obtained without substantial increase of a driving voltage.

The electron transport region ETR may include a hole blocking layer as described above. The hole blocking layer may include, for example, 2,9-dimethyl-4,7-diphenyl-1,10-phenanthroline (BCP), or 4,7-diphenyl-1,10-phenanthroline (Bphen).

A second electrode EL2 is provided on the electron transport region ETR. The second electrode EL2 may be a common electrode or a cathode. The second electrode EL2 may be a transmissive electrode, a transflective electrode or a reflective electrode. If the second electrode EL2 is a transmissive electrode, the second electrode EL2 may include a transparent metal oxide, for example, ITO, IZO, ZnO, ITZO, etc.

If the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound including thereof, or a mixture thereof (for example, a mixture of Ag and Mg). The second electrode EL2 may have a multilayered structure including a reflective layer or a transflective layer formed using the above-described materials and a transparent conductive layer formed using ITO, IZO, ZnO, ITZO, etc.

The second electrode EL2 may be connected with an auxiliary electrode. If the second electrode EL2 is connected with the auxiliary electrode, the resistance of the second electrode EL2 may be decreased.

In the organic electroluminescence device 10, according to the application of a voltage to each of the first electrode EL1 and second electrode EL2, holes injected from the first electrode EL1 may move via the hole transport region HTR to the emission layer EML, and electrons injected from the second electrode EL2 may move via the electron transport region ETR to the emission layer EML. The electrons and the holes may be recombined in the emission layer EML to produce excitons, and the excitons may emit light via transition from an excited state to a ground state.

If the organic electroluminescence device 10 is a top emission type, the first electrode EL1 may be a reflective electrode and the second electrode EL2 may be a transmissive electrode or a transflective electrode. If the organic electroluminescence device 10 is a bottom emission type, the first electrode EL1 may be a transmissive electrode or a transflective electrode and the second electrode EL2 may be a reflective electrode.

The organic electroluminescence device according to an embodiment includes the polycyclic compound represented by Formula 1. Thus, high emission efficiency may be secured and at the same time, the probability of generating the roll-off phenomenon of the organic electroluminescence device may be minimized. The polycyclic compound according to an embodiment may be used as the dopant material of an emission layer. A high emission efficiency of an organic electroluminescence device may be achieved and the generation of the roll-off phenomenon of an organic electroluminescence device may be restrained.

For example, a bulky substituent having a large volume such as a t-butyl group may be substituted at carbon position 2 of a pyrene core represented by Formula 1, and carbazolyl groups may be symmetrically connected at carbon positions 6 and 8 of the pyrene core. Due to the above-described structure of the polycyclic compound represented by Formula 1, the transition from a high triplet excitation state (Tn) (n is an integer of 3 or more) to a triplet excitation state having a lower energy level (Tn-1, Tn-2, Tn-3. . . etc.) may be restrained. Accordingly, the transition from a high triplet excitation state to an adjacent singlet excitation state may be induced in the polycyclic compound according to an embodiment. For example, the transition (K2) of the fourth triplet excitation state (T4) and an adjacent singlet excitation state (S1) of the polycyclic compound according to an embodiment may be induced as shown in FIG. 1.

In the organic electroluminescence device according to an embodiment, reverse intersystem crossing to a singlet excitation state may occur using a triplet excitation state having a high energy level (Tn: for example, T3 or T4). Deep blue emission with high efficiency may be accomplished, and the probability of generating the roll-off phenomenon of the organic electroluminescence device may be minimized.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

SYNTHETIC EXAMPLES

1. Synthesis of Compound 1

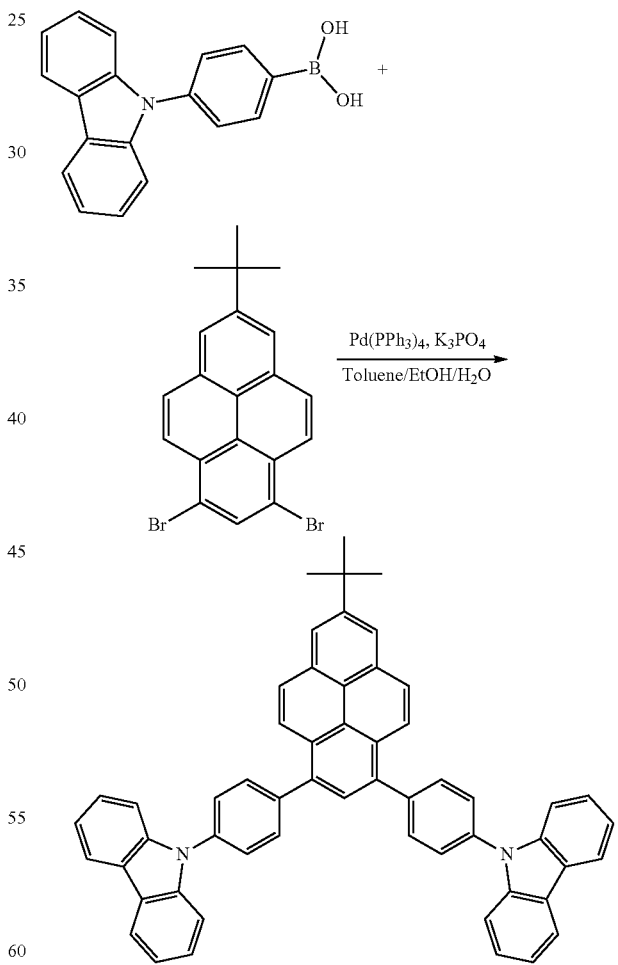

Under an argon (Ar) atmosphere, to a 200 ml three-neck flask, 1.60 g of 4-(N-carbazolyl)phenylboronic acid, 1.13 g of 1,3-dibromo-7-tert-butylpyrene, 2.50 g of $K_3PO_4$, 0.35 g of $Pd(PPh_3)_4$, mixed solution of Toluene/EtOH/$H_2O_5$ were added, followed by heating and refluxing for about 12 hours. After cooling in the air, a solvent layer was separated and removed, solids precipitated in an organic layer were filtered, and 1.20 g (yield 60%) of Compound 1 as a yellow powder was obtained. The molecular weight of Compound 1 measured by FAB-MS was 741. In addition, chemical shift values of the compound measured by $^1$H-NMR (300 MHz, tetrahydrofuran-d8) were 8.38-8.42 (m,4H), 8.17-8.22 (m,7H), 8.03 (d,4H), 7.66 (d,4H), 7.60 (d,4H), 7.43 (t,4H), 7.27 (t,4H), 1.62 (s,9H). From the results, the compound of the yellow powder was identified as Compound 1.

2. Synthesis of Compound 2

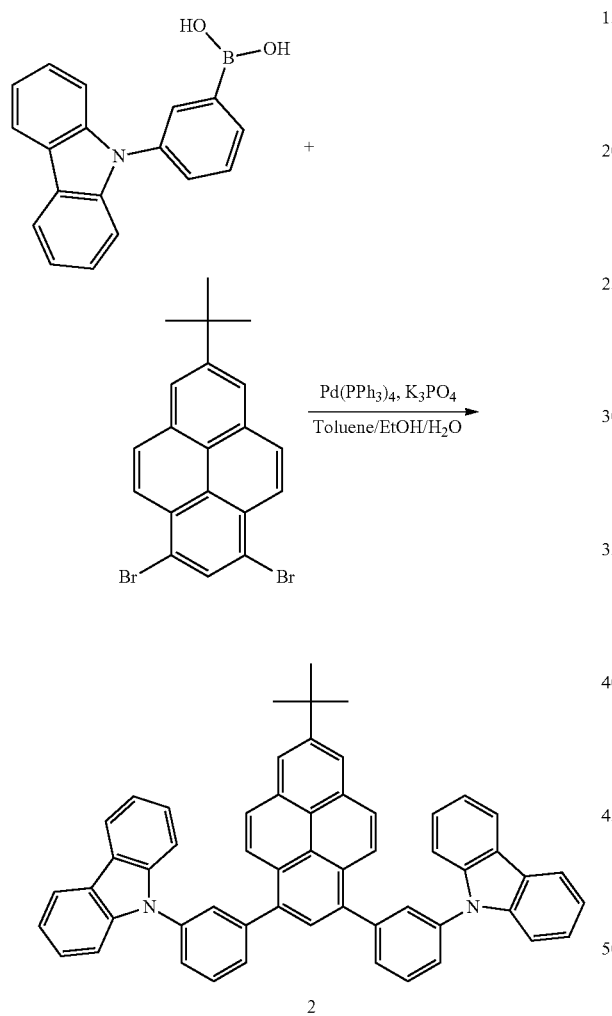

Under an argon (Ar) atmosphere, to a 200 ml three-neck flask, 2.00 g of 3-(N-carbazolyl)phenylboronic acid, 1.39 g of 1,3-dibromo-7-tert-butylpyrene, 2.96 g of $K_3PO_4$, 0.40 g of $Pd(PPh_3)_4$, mixed solution of Toluene/EtOH/$H_2O$ were added, followed by heating and refluxing for about 7 hours. After cooling in the air, an organic layer was separately taken and solvents were evaporated under a reduced pressure. The crude product thus obtained was separated by silica gel column chromatography (using toluene) to obtain 2.08 g (yield 82%) of Compound 2 as a yellow powder. The molecular weight of Compound 2 measured by FAB-MS was 741. In addition, chemical shift values of the compound measured by $^1$H-NMR (300 MHz, tetrahydrofuran-d8) were 8.42-8.37 (m,4H), 8.23-8.15 (m,7H), 8.01 (d,2H), 7.90-7.87 (m,4H), 7.81-7.76 (m,2H), 7.59 (d,4H), 7.39 (t,4H), 7.25 (t,4H), 1.63 (s,9H). From the results, the compound of the yellow powder was identified as Compound 2.

3. Synthesis of Compound 3

Synthesis of Compound A

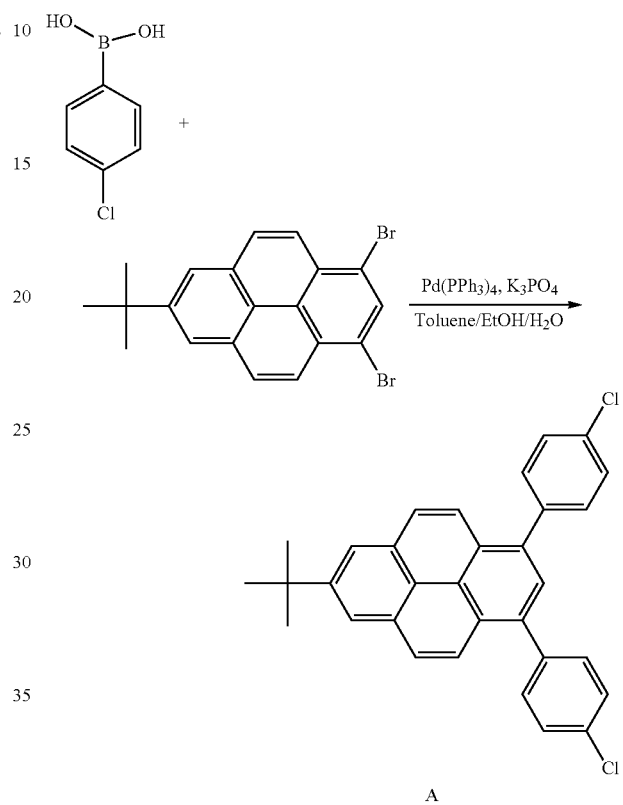

Under an argon (Ar) atmosphere, to a 200 ml three-neck flask, 2.00 g of 4-chlorophenylboronic acid, 2.55 g of 1,3-dibromo-7-tert-butylpyrene, 5.43 g of $K_3PO_4$, 0.74 g of $Pd(PPh_3)_4$, mixed solution of Toluene/EtOH/$H_2O$ were added, followed by heating and refluxing for about 12 hours. After cooling in the air, an organic layer was separately taken and solvents were evaporated under a reduced pressure. The crude product thus obtained was separated by silica gel column chromatography (using toluene) to obtain 2.60 g (yield 88%) of Compound A as a white powder.

Synthesis of Compound 3

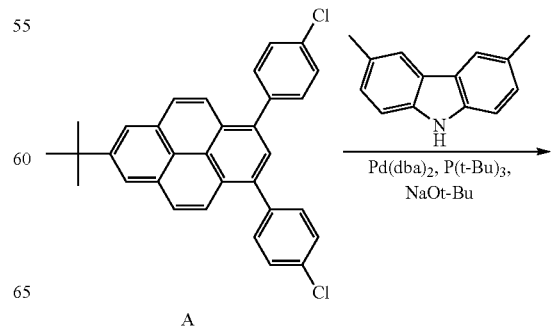

-continued

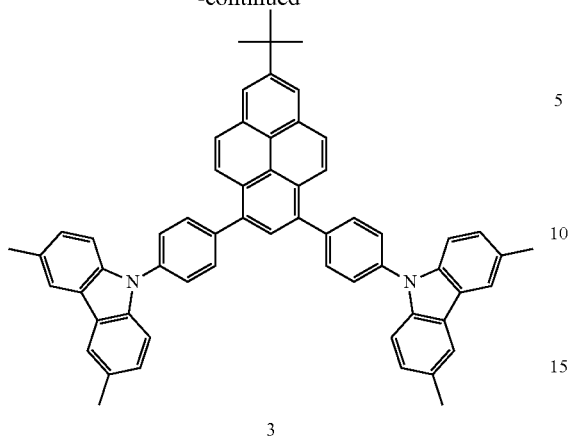

3

Under an argon (Ar) atmosphere, in a 100 ml three-neck flask, 0.93 g of 3,6-dimethylcarbazole, 1.09 g of Compound A, 0.88 g of sodium tert-butoxide, 0.13 g of Pd(dba)$_2$, 0.15 ml of P(t-Bu)$_3$, and 40 ml of anhydrous xylene were mixed, followed by heating and refluxing for about 5 hours. After cooling in the air, an organic layer was separately taken and solvents were evaporated under a reduced pressure. The crude product thus obtained was separated by silica gel column chromatography (using toluene) to obtain 1.79 g (yield 98%) of Compound 3 as a yellow powder. The molecular weight of Compound 3 measured by FAB-MS was 797. In addition, chemical shift values of the compound measured by $^1$H-NMR (300 MHz, tetrahydrofuran-d8) were 8.17-8.20 (m,4H), 8.03 (d,4H), 8.17 (s,1H), 7.95-8.00 (m,8H), 7.85 (d,4H), 7.49 (t,4H), 7.25 (t,4H), 2.54 (s,12H), 1.62 (s,9H). From the results. the compound of the yellow powder was identified as Compound 3.

EXPERIMENTAL EXAMPLES

Device Manufacturing Examples

An organic electroluminescence device of Example 1 was manufactured using
Compound 1 as a dopant material for an emission layer.
[Example Compound]

1

Comparative Compound C1 was used in the organic electroluminescence device of Comparative Example 1.

[Comparative Compound]

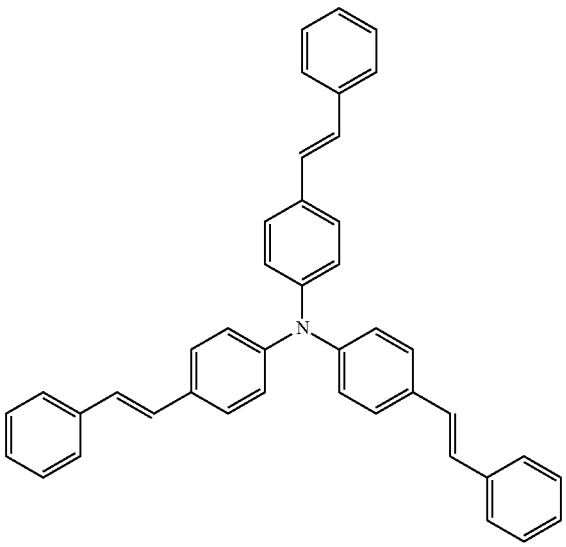

C1

Organic electroluminescence devices of Example 1 and Comparative Example 1 were manufactured by forming a first electrode using ITO to a thickness of about 150 nm, a first hole transport layer using 4,4'-cyclohexylidene bis[N,N-bis(4-methylphenyl)benzamine] (TAPC) to a thickness of about 80 nm, a second hole transport layer using 1,3-bis(N-carbazolyl)benzene (mCP) to a thickness of about 5 nm, an emission layer using 10,10'-diphenyl-10H,10'H-9,9'-spirobi[acridine] doped with 24% of the example compound or the comparative compound to a thickness of about 20 nm, an electron transport layer using 3,3'',5,5''-tetra(pyridin-3-yl)-1,1':3',1''-terphenyl (BmPyPhB) to a thickness of about 40 nm, an electron injection layer using LiF to a thickness of about 1 nm, and a second electrode using Al to a thickness of about 100 nm. Each layer was formed by a deposition method in vacuum.

EXPERIMENTAL EXAMPLES

The maximum emission wavelength, the external quantum efficiency (EQE), and the color coordinate of each of the organic electroluminescence devices according to Example 1 and Comparative Example 1 were evaluated. In addition, the generation of delayed light emission in each of the example and the comparative example was checked. The evaluation results are listed in Table 1 below. The external quantum efficiency of each of the example and the comparative example is a value measured at a current density of about 10 mA/cm$^2$.

TABLE 1

| Device manufacturing example | Dopant | Maximum emission wavelength (nm) | External quantum efficiency (%) | Color coordinate CIE (x, y) | Generation of delayed light emission |
|---|---|---|---|---|---|
| Example 1 | Example Compound 1 | 440 | 5.7 | 0.152, 0.06 | ○ |
| Comparative Example 1 | Comparative Compound C1 | 470 | 4.8 | 0.140, 0.173 | X |

Referring to the results in Table 1, it can be seen that Example 1 emitted light with lower wavelength, i.e., blue light deeper than Comparative Example 1, and had increased external quantum efficiency. Example 1 showed external quantum efficiency greater by about 5% of the maximum theoretical efficiency of an organic electroluminescence device which emitted fluorescence.

The generation of delayed light emission was measured in Example 1. When an emission layer doped with the host of Example Compound 1 was irradiated with light and when time analysis light emission spectrum was measured by a streak camera, delayed light emission, $\tau_2=31$ ns and $\tau_3=157$ ns, was measured in addition to a common fluorescence component ($\tau_1<1$ ns).

The delayed light emission measured in Example 1 showed a long light emission time that was tens to hundreds times the light emission time ($\tau_1$) of a common fluorescence material, and showed a short light emission time that was tens to hundreds times the light emission time ($\tau_n>1$ μs) of a phosphorescence material or a thermally activated delayed fluorescence (TADF) material.

Through the delayed light emission measured in Example 1, as explained in FIG. 1, reverse intersystem crossing (RISC) of triplet excitons to singlet excitons was generated using a high triplet excitation state (for example, T3 or T4) having a high energy level in Example Compound 1 which was applied in Example 1. In Example Compound 1 included in Example 1, a bulky substituent having a large volume such as a t-butyl group was substituted at the carbon of position 2 in a pyrene core, and carbazolyl groups were symmetrically connected at carbons of positions 6 and 8 in the pyrene core. Thus, the transition from a high triplet excitation state to a triplet excitation state having a lower energy level was restrained. Accordingly, the transition from a high triplet excitation state to an adjacent singlet excitation state was induced, and thus, delayed light emission of which light emission time was longer than a common fluorescence material and shorter than a phosphorescence material or a TADF material, was generated.

In Example 1, reverse intersystem crossing from a high triplet excitation state to an adjacent singlet excitation state was induced, and light emission with high efficiency greater than theoretical efficiency of a common fluorescence emission device was possible. In addition, the light emission time was shorter than a TADF material, and heat was not required. Accordingly, the probability of generating a roll-off phenomenon of an organic electroluminescence device was minimized.

Comparative Compound C1 included in Comparative Example 1 did not include a pyrene core and included a carbazolyl group different from the Example Compound. Accordingly, the transition from a high triplet excitation state to a triplet excitation state that had a lower energy level was not restrained. Therefore, the emission efficiency of Comparative Example 1 was lower than Example 1.

By way of summation and review, organic electroluminescence devices are classified into a fluorescence organic electroluminescence device and a phosphorescence electroluminescence device according to emission principles. The fluorescence organic electroluminescence device has limits in that it is difficult for external quantum efficiency to exceed about 5%. The phosphorescence organic electroluminescence device has limits in that driving durability is weak. In order to improve the limits of the general fluorescence organic electroluminescence device and the phosphorescence organic electroluminescence device, a fluorescence organic electroluminescence device using triplet-triplet annihilation (TTA) by which singlet excitons are produced by the collision of triplet excitons, and a fluorescence organic electroluminescence device using thermally activated delayed fluorescence (TADF), etc. have been suggested.

The organic electroluminescence device including the polycyclic compound according to an embodiment may achieve high emission efficiency and long life.

The polycyclic compound according to an embodiment may have extremely small thermal energy requirement for transforming a triplet to a singlet. If applied to an organic electroluminescence device, the generation ratio of roll-off phenomenon may be minimized.

The organic electroluminescence device according to an embodiment may achieve high efficiency and also provide a reduction of roll-off.

An organic electroluminescence device according to an embodiment may include a first electrode, a hole transport region disposed on the first electrode, an emission layer disposed on the hole transport region, an electron transport region disposed on the emission layer, and a second electrode disposed on the electron transport region. The emission layer may include the polycyclic compound represented by Formula 1.

In an embodiment, the emission layer may include a host and a dopant. The dopant may include the polycyclic compound represented by Formula 1.

In an embodiment, the lowest triplet excitation energy level of the host may be about 3 eV or more, and the lowest triplet excitation energy level of the host may be higher than the lowest singlet excitation energy level of the dopant.

In an embodiment, the polycyclic compound may generate reverse intersystem crossing (RISC) from a high triplet excitation energy level higher than the lowest triplet excitation energy level to a singlet excitation energy level.

In an embodiment, the maximum emission wavelength of the emission layer may be about 480 nm or less.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope thereof t as set forth in the following claims.

What is claimed is:

1. A polycyclic compound represented by the following Formula 1:

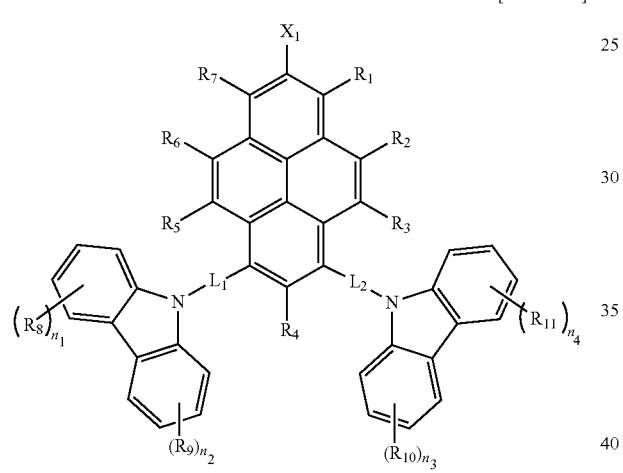

[Formula 1]

in Formula 1, $X_1$ is a substituted or unsubstituted triphenylsilyl group, $R_1$ to $R_{11}$ are each independently a hydrogen atom, a deuterium atom, a halogen atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, $L_1$ and $L_2$ are each independently a substituted or unsubstituted arylene group having 6 to 30 ring carbon atoms, and "$n_1$" to "$n_4$" are each independently an integer of 0 to 4, and wherein the polycyclic compound is symmetric.

2. The polycyclic compound as claimed in claim 1, wherein the polycyclic compound represented by Formula 1 is represented by the following Formula 2:

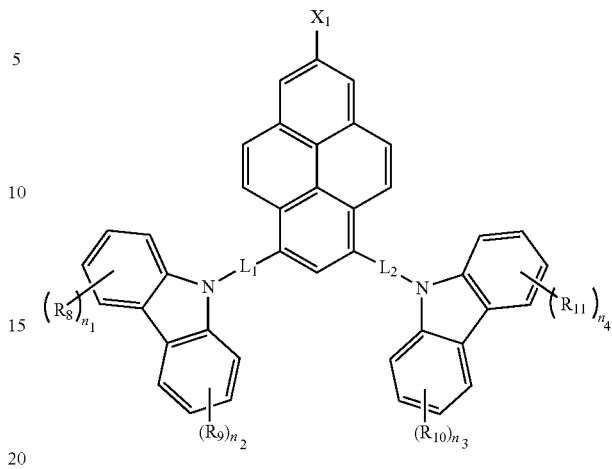

[Formula 2]

in Formula 2, $X_1$, $L_1$, $L_2$, $R_8$ to $R_{11}$, and "$n_1$" to "$n_4$" are the same as defined in Formula 1.

3. The polycyclic compound as claimed in claim 2, wherein the polycyclic compound represented by Formula 2 is represented by the following Formula 3:

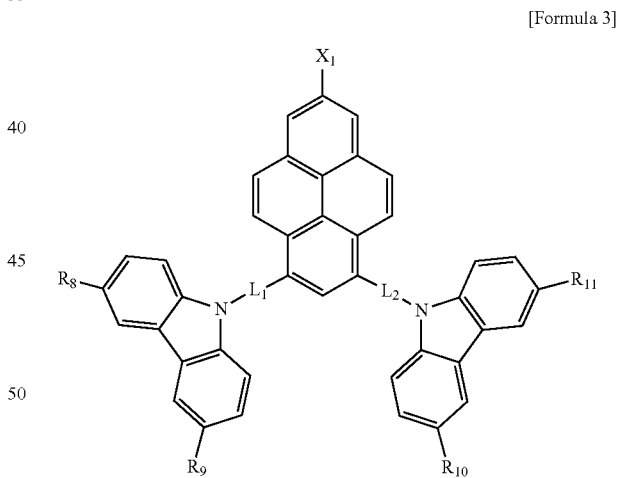

[Formula 3]

in Formula 3, $X_1$, $L_1$, $L_2$, and $R_8$ to $R_{11}$ are the same as defined in Formula 1.

4. The polycyclic compound as claimed in claim 3, wherein, in Formula 3, $L_1$ and $L_2$ are the same, $R_8$ and $R_{11}$ are the same, and $R_9$ and $R_{10}$ are the same.

5. The polycyclic compound as claimed in claim 3, wherein the polycyclic compound is represented by Formula 3 is further represented by the following Formula 4:

[Formula 4]

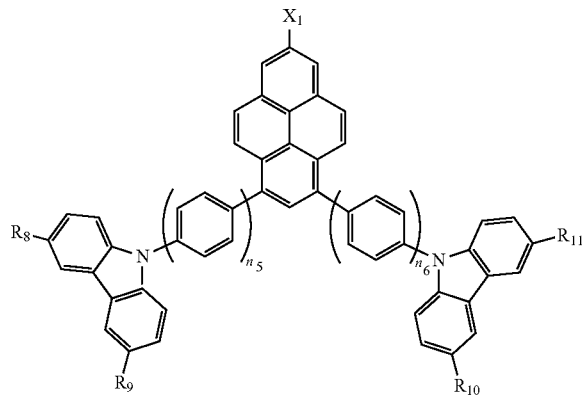

in Formula 4,

"$n_5$" and "$n_6$" are each independently 1 or 2, and $X_1$, and $R_8$ to $R_{11}$ are the same as defined in Formula 1.

6. The polycyclic compound as claimed in claim 1, wherein $R_8$ to $R_{11}$ are each independently a halogen atom, a substituted or unsubstituted methyl group, or a substituted or unsubstituted phenyl group.

7. The polycyclic compound as claimed in claim 1, wherein $L_1$ and $L_2$ are each independently a substituted or unsubstituted phenylene group, or a substituted or unsubstituted divalent biphenyl group.

8. The polycyclic compound as claimed in claim 1, wherein the polycyclic compound represented by Formula 1 is one selected from compounds represented in the following Compound Group 1:

[Compound Group 1]

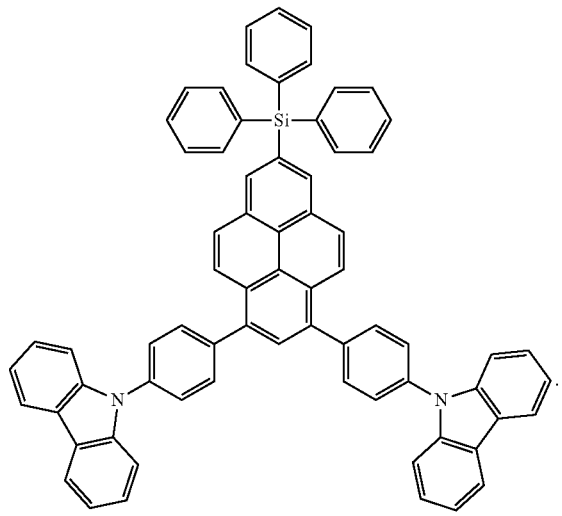

9. A polycyclic compound represented by the following Formula 5:

[Formula 5]

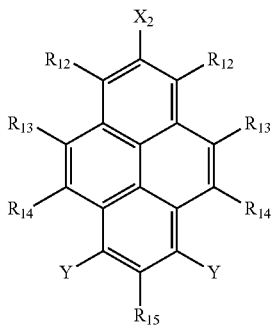

in Formula 5, $X_2$ is a substituted or unsubstituted triphenylsilyl group, $R_{12}$ to $R_{15}$ are each independently a hydrogen atom, a deuterium atom, a halogen atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, and each Y is represented by the following Formula 6:

[Formula 6]

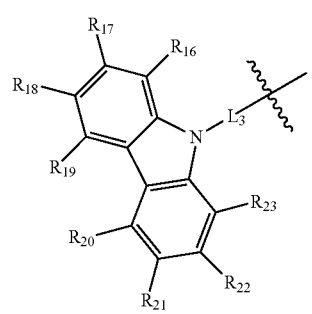

in Formula 6, $L_3$ is a substituted or unsubstituted arylene group having 6 to 30 ring carbon atoms, $R_{16}$ to $R_{23}$ are each independently a hydrogen atom, a deuterium atom, a halogen atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, and wherein the polycyclic compound is symmetric.

10. An organic electroluminescence device, comprising:

a first electrode;

a hole transport region on the first electrode;

an emission layer on the hole transport region;

an electron transport region on the emission layer; and a second electrode on the electron transport region, wherein the emission layer includes a polycyclic compound represented by the following Formula 1:

[Formula 1]

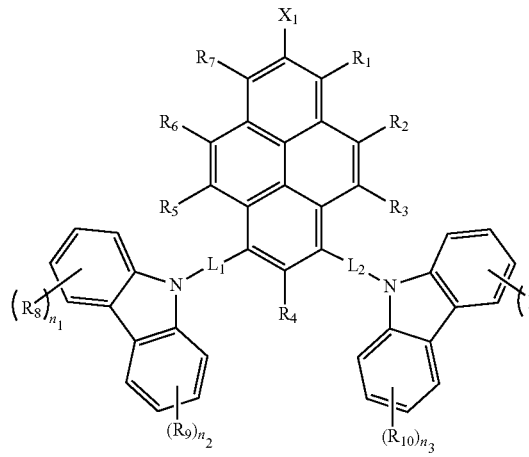

in Formula 1, $X_1$ is a substituted or unsubstituted triphenylsilyl group, $R_1$ to $R_{11}$ are each independently a hydrogen atom, a deuterium atom, a halogen atom, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, $L_1$ and $L_2$ are each independently a substituted or unsubstituted arylene group having 6 to 30 ring carbon atoms, and "$n_1$" to "$n_4$" are each independently an integer of 0 to 4, and wherein the polycyclic compound is symmetric.

11. The organic electroluminescence device as claimed in claim 10, wherein: the emission layer includes a host and a dopant, and the dopant includes the polycyclic compound represented by Formula 1.

12. The organic electroluminescence device as claimed in claim 11, wherein a lowest triplet excitation energy level of the host is about 3 eV or more, and the lowest triplet excitation energy level of the host is higher than a lowest singlet excitation energy level of the dopant.

13. The organic electroluminescence device as claimed in claim 10, wherein a maximum emission wavelength of the emission layer is about 480 nm or less.

14. The organic electroluminescence device as claimed in claim 10, wherein the polycyclic compound represented by Formula 1 is represented by the following Formula 2:

[Formula 2]

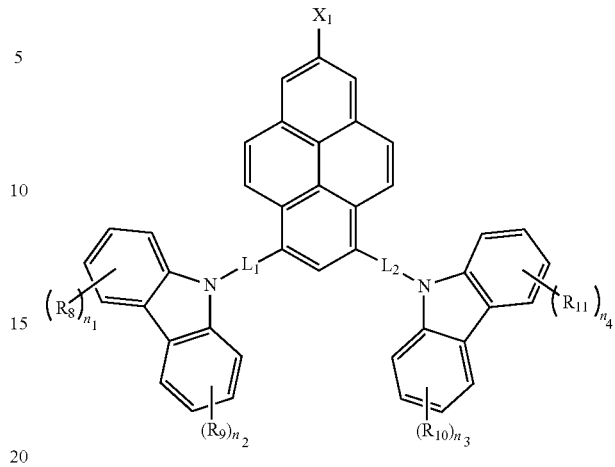

in Formula 2, $X_1$, $L_1$, $L_2$, $R_8$ to $R_{11}$, and "$n_1$" to "$n_4$" are the same as defined in Formula 1.

15. The organic electroluminescence device as claimed in claim 14, wherein the polycyclic compound represented by Formula 2 is represented by the following Formula 3:

[Formula 3]

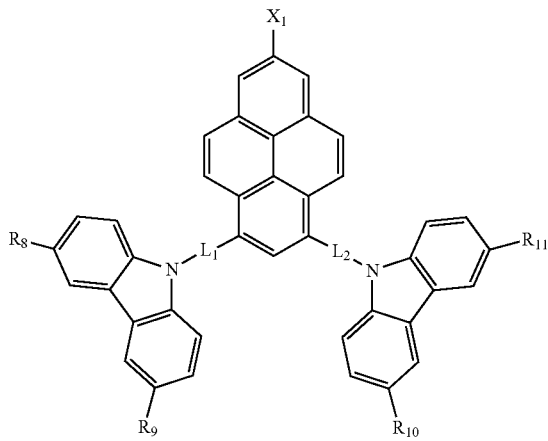

in Formula 3, $X_1$, $L_1$, $L_2$, and $R_8$ to $R_{11}$ are the same as defined in Formula 1.

16. The organic electroluminescence device as claimed in claim 15, wherein $L_1$ and $L_2$ are the same, $R_8$ and $R_{11}$ are the same, and $R_9$ and $R_{10}$ are the same.

17. The organic electroluminescence device as claimed in claim 15, wherein the polycyclic compound represented by Formula 3 is represented by the following Formula 4:

[Formula 4]

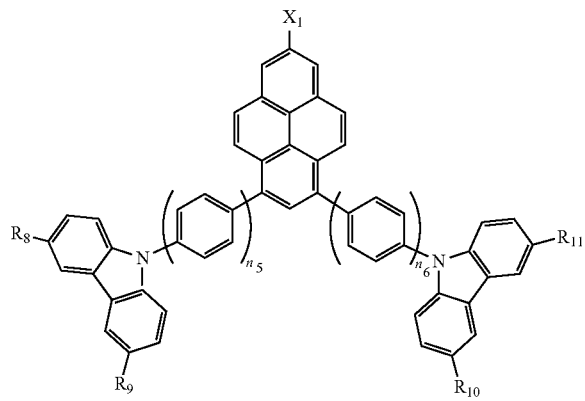

in Formula 4,
"$n_5$" and "$n_4$" are each independently 1 or 2, and
$X_1$, and $R_8$ to $R_{11}$ are the same as defined in Formula 1.

18. The organic electroluminescence device as claimed in claim 10, wherein $R_8$ to $R_{11}$ are each independently a halogen atom, a substituted or unsubstituted methyl group, or a substituted or unsubstituted phenyl group.

19. The organic electroluminescence device as claimed in claim 10, wherein $L_1$ and $L_2$ are each independently a substituted or unsubstituted phenylene group, or a substituted or unsubstituted divalent biphenyl group.

20. The organic electroluminescence device as claimed in claim 10, wherein the polycyclic compound represented by Formula 1 is one selected from compounds represented in the following Compound Group 1:

[Compound Group 1]

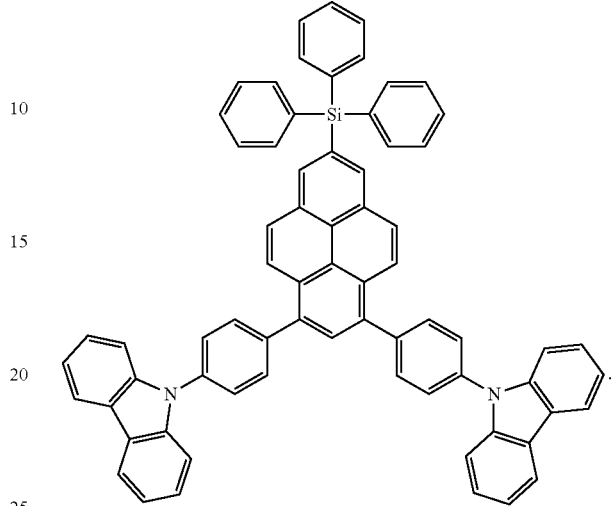

21. The organic electroluminescence device as claimed in claim 10, wherein the polycyclic compound generates reverse intersystem crossing from a high triplet excitation energy level higher than the lowest triplet excitation energy level to a singlet excitation energy level.

* * * * *